United States Patent
Gehrke et al.

(10) Patent No.: US 11,638,559 B2
(45) Date of Patent: May 2, 2023

(54) SLEEPING OR RECLINING FURNITURE WITH A SENSOR

(71) Applicant: DewertOkin GmbH, Kirchlengern (DE)

(72) Inventors: Karsten Gehrke, Porta Westfalica (DE); Armin Hille, Bielefeld (DE); Steffen Loley, Osnabrück (DE); Alexander Tews, Bielefeld (DE)

(73) Assignee: DEWERTOKIN TECHNOLOGY GROUP CO., LTD

( * ) Notice: Subject to any disclaimer, the term of this patent is extended or adjusted under 35 U.S.C. 154(b) by 1112 days.

(21) Appl. No.: 16/067,519

(22) PCT Filed: Dec. 30, 2016

(86) PCT No.: PCT/EP2016/082921
§ 371 (c)(1),
(2) Date: Jun. 29, 2018

(87) PCT Pub. No.: WO2017/114950
PCT Pub. Date: Jul. 6, 2017

(65) Prior Publication Data
US 2020/0383854 A1  Dec. 10, 2020

(30) Foreign Application Priority Data

Dec. 30, 2015 (DE) .................. 20 2015 107 148.5
May 24, 2016 (DE) .................. 10-2016 109 524.9
(Continued)

(51) Int. Cl.
*A61B 5/00* (2006.01)
*A47C 21/00* (2006.01)
(Continued)

(52) U.S. Cl.
CPC .......... *A61B 5/6892* (2013.01); *A47C 17/162* (2013.01); *A47C 17/163* (2013.01);
(Continued)

(58) Field of Classification Search
CPC ..... A61B 5/6892; A61B 5/113; A61B 5/0022; A61B 5/1123; A61B 5/4809; A61B 5/746;
(Continued)

(56) References Cited

U.S. PATENT DOCUMENTS 3,926,177 A * 12/1975 Hardway, Jr. .......... A61B 5/113
  600/535
4,012,604 A *  3/1977 Speidel .................. A61B 5/021
  367/180
(Continued)

FOREIGN PATENT DOCUMENTS

CN  1741782 A   3/2006
CN  1980602 A   6/2007
(Continued)

OTHER PUBLICATIONS

Chinese Search Report dated Jun. 15, 2020 with respect to counterpart Chinese patent application 201680081742.9.
(Continued)

*Primary Examiner* — Myles A Throop
(74) *Attorney, Agent, or Firm* — Henry M. Feiereisen LLC

(57) ABSTRACT

The invention relates to a piece of sleeping or reclining furniture, comprising a support element (2) for applying a padding or a mattress and at least one sensor (12) for detecting vibrations, movement, and/or sound. The piece of sleeping or reclining furniture is characterized in that the at least one sensor (12) is arranged at a section (120) of the support element (2) that is decoupled from further sections
(Continued)

of the support element (2) and/or of the sleeping or reclining furniture.

10 Claims, 16 Drawing Sheets

(30) Foreign Application Priority Data

Jul. 6, 2016 (DE) .................. 20 2016 103 605.4
Oct. 7, 2016 (DE) .................. 20 2016 105 635.7

(51) Int. Cl.

| | | |
|---|---|---|
| A47C 31/00 | (2006.01) | |
| A61B 5/0205 | (2006.01) | |
| A61B 5/113 | (2006.01) | |
| A47C 27/00 | (2006.01) | |
| A61G 7/05 | (2006.01) | |
| A61G 7/075 | (2006.01) | |
| A61G 7/10 | (2006.01) | |
| A61G 7/16 | (2006.01) | |
| A61G 13/08 | (2006.01) | |
| A61G 7/018 | (2006.01) | |
| A61G 13/02 | (2006.01) | |
| A61G 7/015 | (2006.01) | |
| A47C 20/04 | (2006.01) | |
| A47C 17/16 | (2006.01) | |
| A47C 19/02 | (2006.01) | |
| A61B 5/11 | (2006.01) | |
| G05B 19/416 | (2006.01) | |
| A61B 5/024 | (2006.01) | |
| A61B 5/08 | (2006.01) | |

(52) U.S. Cl.
CPC .......... *A47C 19/027* (2013.01); *A47C 20/041* (2013.01); *A47C 21/003* (2013.01); *A47C 27/00* (2013.01); *A47C 31/00* (2013.01); *A47C 31/008* (2013.01); *A61B 5/002* (2013.01); *A61B 5/0022* (2013.01); *A61B 5/0205* (2013.01); *A61B 5/113* (2013.01); *A61B 5/1116* (2013.01); *A61B 5/1123* (2013.01); *A61B 5/1135* (2013.01); *A61B 5/4806* (2013.01); *A61B 5/4809* (2013.01); *A61B 5/6891* (2013.01); *A61B 5/725* (2013.01); *A61B 5/746* (2013.01); *A61G 7/015* (2013.01); *A61G 7/018* (2013.01); *A61G 7/0506* (2013.01); *A61G 7/0524* (2016.11); *A61G 7/0755* (2013.01); *A61G 7/1065* (2013.01); *A61G 7/16* (2013.01); *A61G 13/02* (2013.01); *A61G 13/08* (2013.01); *G05B 19/416* (2013.01); *A61B 5/024* (2013.01); *A61B 5/02444* (2013.01); *A61B 5/0816* (2013.01); *A61G 2200/327* (2013.01); *A61G 2200/34* (2013.01); *G05B 2219/43196* (2013.01)

(58) Field of Classification Search
CPC ..... A61B 5/002; A61B 5/1116; A61B 5/6891; A61B 5/0205; A61B 5/1135; A61B 5/4806; A61B 5/725; A61B 5/02444; A61B 5/024; A61B 5/0816; A61G 7/0506; A61G 7/0755; A61G 7/1065; A61G 7/16; A61G 2200/327; A61G 2200/34; A47C 31/00; A47C 27/00; A47C 17/162; A47C 17/163; A47C 19/027; A47C 21/003; A47C 31/008; A47C 20/041; G05B 19/416; G05B 2219/43196
See application file for complete search history.

(56) References Cited

U.S. PATENT DOCUMENTS

| | | | | |
|---|---|---|---|---|
| 4,595,023 A * | 6/1986 | Bonnet | ............... | A61B 5/1102 27/31 |
| 4,677,857 A * | 7/1987 | Feldmann | ............... | F16B 5/02 403/24 |
| 5,271,412 A * | 12/1993 | Shtalryd | ............... | A61B 5/113 600/534 |
| 6,011,477 A * | 1/2000 | Teodorescu | ............ | A61B 5/113 340/573.1 |
| 6,146,332 A * | 11/2000 | Pinsonneault | ........ | A61B 5/113 600/534 |
| 6,491,647 B1 * | 12/2002 | Bridger | ............... | G01L 1/2231 128/900 |
| 6,661,161 B1 * | 12/2003 | Lanzo | ............... | A61B 7/00 310/334 |
| 7,306,564 B2 * | 12/2007 | Nakatani | ............... | A61B 5/103 600/529 |
| 8,281,433 B2 * | 10/2012 | Riley | ............... | A61G 7/0514 5/600 |
| 9,836,034 B2 * | 12/2017 | Hille | ............... | G05B 15/02 |
| 10,149,549 B2 * | 12/2018 | Erko | ............... | A47C 27/082 |
| 2005/0190065 A1 * | 9/2005 | Ronnholm | ............ | G04G 21/025 340/575 |
| 2006/0241510 A1 * | 10/2006 | Halperin | ............... | A61B 5/7275 600/534 |
| 2008/0005838 A1 | 1/2008 | Wan Fong et al. | | |
| 2008/0140349 A1 * | 6/2008 | Behera | ............... | G05B 23/0283 702/182 |
| 2008/0269625 A1 * | 10/2008 | Halperin | ............... | A61B 5/08 600/508 |
| 2008/0306396 A1 * | 12/2008 | Ariav | ............... | A61B 5/113 600/595 |
| 2010/0101022 A1 | 4/2010 | Riley et al. | | |
| 2010/0256512 A1 * | 10/2010 | Sullivan | ............... | G01H 11/00 600/529 |
| 2012/0138067 A1 * | 6/2012 | Rawls-Meehan | ....... | G16Z 99/00 128/845 |
| 2012/0253142 A1 | 10/2012 | Meger et al. | | |
| 2012/0344675 | 10/2012 | Meger et al. | | |
| 2015/0019020 A1 * | 1/2015 | Hille | ............... | G05B 15/02 700/275 |
| 2015/0025688 A1 | 1/2015 | Hille et al. | | |
| 2015/0026890 A1 | 1/2015 | Hille et al. | | |
| 2015/0035457 A1 | 2/2015 | Hille et al. | | |
| 2015/0241857 A1 | 8/2015 | Hille | | |
| 2016/0081866 A1 | 3/2016 | Hille | | |
| 2016/0377273 A1 | 12/2016 | Hille | | |
| 2017/0128296 A1 * | 5/2017 | Kostic | ............... | A61G 7/0507 |
| 2019/0008283 A1 * | 1/2019 | Gehrke | ............... | A47C 17/163 |
| 2019/0021675 A1 * | 1/2019 | Gehrke | ............... | A47C 21/003 |
| 2021/0174613 A1 * | 6/2021 | Fischer | ............... | G07C 5/0808 |
| 2021/0227311 A1 * | 7/2021 | Minarsch | ............... | H04R 1/1041 |

FOREIGN PATENT DOCUMENTS

| | | |
|---|---|---|
| CN | 101960797 A | 1/2011 |
| CN | 104254275 A | 12/2014 |
| JP | 2004-344675 A | 12/2004 |
| JP | 2005-177471 A | 7/2005 |
| JP | 2005-253957 | 9/2005 |
| WO | WO 2013/173640 A1 | 11/2013 |

OTHER PUBLICATIONS

Translation of Chinese Search Report dated Jun. 15, 2020 with respect to counterpart Chinese patent application 201680081742.9.
International Search Report issued by the European Patent Office in International Application PCT/EP2016/082921 dated Mar. 21, 2017.
Armin Hille et al, U.S. Pat. No. 9,792,810, Oct. 17, 2017, 2016-0275785-A1, Sep. 22, 2016.
Armin Hille, U.S. Pat. No. 9,478,122, Oct. 25, 2016, 2015-0130595-A1, May 14, 2015.

(56) References Cited

OTHER PUBLICATIONS

Armin Hille et al, U.S. Pat. No. 9,836,034, Dec. 5, 2017, 2015-0019020-A1, Jan. 15, 2015.
Armin Hille, U.S. Pat. No. 9,713,387, Jul. 25, 2017, 2015-0048763-A1, Feb. 19, 2015.
Armin Hille, U.S. Pat. No. 9,715,822, Jul. 25, 2017, 2015-0123772-A1, May 7, 2015.
Armin Hille, U.S. Pat. No. 9,252,692, Feb. 2, 2016, 2014-0159618-A1, Jun. 12, 2014.
Armin Hille, U.S. Pat. No. 9,331,610, May 3, 2016, 2014-0152068, Jun. 5, 2014.
Armin Hille, U.S. Pat. No. 9,230,764, Jan. 5, 2016, 2012-0194106, Aug. 2, 2012.

\* cited by examiner

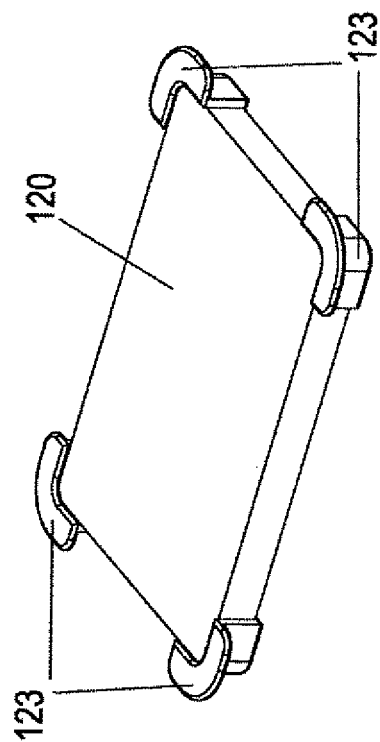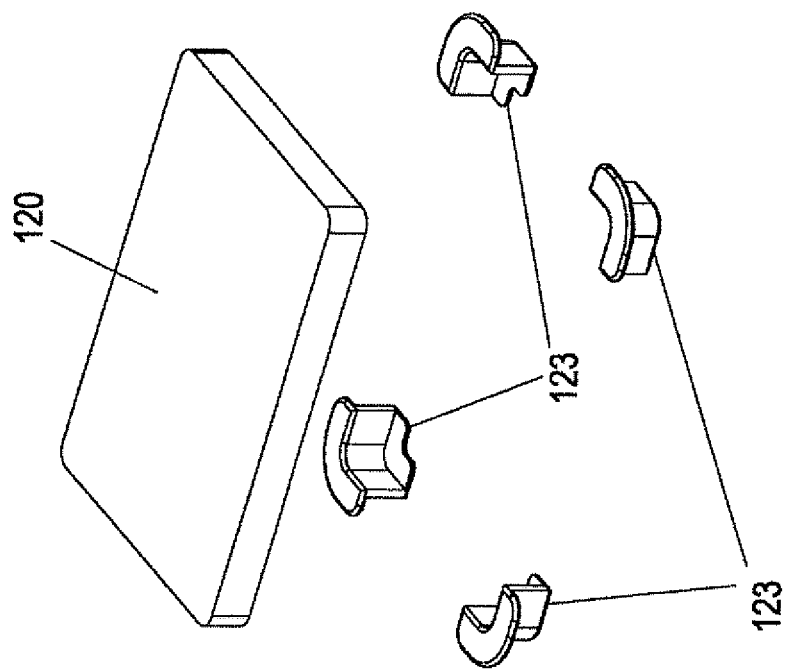

SLEEPING OR RECLINING FURNITURE WITH A SENSOR

CROSS-REFERENCES TO RELATED APPLICATIONS

This application is the U.S. National Stage of International Application No. PCT/EP2016/082921, filed Dec. 30, 2016, which designated the United States and has been published as International Publication NO. WO 2017/114950 and which claims the priorities of German Patent Applications, Serial Nos. 20 2015 107 148.5, filed Dec. 30, 2015, 10 2016 109 524.9, filed May 24, 2016, 20 2016 103 605.4, filed Jul. 6, 2016, and 20 2016 105 635.7, filed Oct. 7, 2016, pursuant to 35 U.S.C. 119(a)-(d).

BACKGROUND OF THE INVENTION

The invention relates to a piece of sleeping or reclining furniture comprising a plate-shaped support element for applying a padding or a mattress and at least one sensor for detecting vibrations, movement, and/or sound.

In the clinical field, monitoring devices are known, which monitor the respiration and/or cardiac activity of a patient in sleep, to be able to engage in the event of worrying cardiac function and circulatory parameters.

In the meantime, devices for monitoring the sleep state on the basis of physiological parameters have also become commercially available for nonclinical purposes. These devices, which are placed on a night table, for example, detect noises and/or movement states during sleep by means of microphones and/or cameras. A sleep state is derived from the detected items of information and the time curve thereof is recorded. The recorded sleep curve can subsequently be retrieved and analyzed. It can be informative about how deep and restful the sleep has been.

In addition to systems which use camera and/or microphone, a sensor-based system is known, in which a pressure-sensitive sensor strip is laid over the mattress and in which the sensor strip is connected to a mobile telephone (smart phone), which records the sensor data. A heart rate and a respiratory rate, inter alia, are derived from the sensor data.

The mentioned nonclinical systems have the disadvantage that the reliability of the recognition is strongly dependent on the correct position of the monitoring devices on a night table and/or on or at the mattress. The reliability and also the usage comfort of these devices are thus restricted.

It is an object of the present invention to provide sleeping or reclining furniture of the type mentioned at the outset, in which further the sensor can reliably be used to monitor the sleeping behavior of a user.

SUMMARY OF THE INVENTION

This object is achieved by a sleeping or reclining furniture having the features of the independent claim. Advantageous embodiments and refinements are specified in the dependent claims.

A piece of sleeping or reclining furniture according to the invention of the type mentioned at the outset is distinguished in that the at least one sensor is arranged at a section of the support element that is decoupled from further sections of the support element and/or of the sleeping or reclining furniture.

The sensor arranged at the support element allows for a convenient and—concerning possible misuse, in particular a misalignment, failsafe system for detecting the physiological parameters. Detected physiological parameters are preferably a heart rate, a respiratory rate, and/or a movement state of the person using the sleeping or reclining furniture. The decoupling, in particular the acoustic decoupling of the section, the sensor is mounted to, a high detection sensitivity is reached. The decoupled section provides a kind of enlarged reception membrane and thus a kind of antenna for the sensor. Accordingly a large vibration amplitude is formed which leads to a strong sensor signal. Furthermore, the acoustic decoupling prevents a transmission of vibrations, which do not origin from the person using the sleeping or reclining furniture, in the form of structure-borne vibrations transmitted via the base of the to the sensor. In particular, a transmission of impact noise, which is transmitted from a floor onto the piece of furniture, is prevented or minimized.

In an advantageous embodiment of the sleeping or reclining furniture, the decoupled section is a plate-shaped part of the support element. In this embodiment, an entire part of a multi-part support element is acoustically decoupled, in particular with regard to a transmission of structure-borne noise, from the remaining parts and/or a frame. This is particularly suitable for smaller ones of the parts of the support element, e.g. a middle part. For decoupling this part can for example be mounted on elastic elements on a frame or framework of the sleeping or reclining furniture. The decoupling can be made directly at the support points of the plate-shaped part. Alternatively, the decoupling may be performed on a support element supporting the plate-shaped member.

In a further advantageous embodiment of the sleeping or reclining furniture, the decoupled section is formed only by a part of a plate-shaped part of the support element. The decoupled section is divided by at least one cut from the plate-shaped part of the support element. The plate-shaped part may be a middle part, a back part or a leg part of the support element.

In one embodiment, a plurality of cuts separated from each other by remaining webs surround the decoupled section, wherein the decoupled section is connected with the surrounding plate-shaped part by the webs only. By the number, positioning and dimensioning of the webs, the vibration characteristics of the decoupled section can be influenced and adjusted so that a good signal strength of the sensor is achieved in such frequency ranges, which are particularly advantageous in determining a user's physiological parameters In an alternative embodiment, a circumferential cut surrounds the decoupled section, wherein the decoupled section is connected by elastic holding or retaining elements with the surrounding plate-shaped part. In this case, the vibration properties of the decoupled section can be influenced and optimally adjusted by the number, positioning, dimensioning and choice of material of the holding elements.

In an advantageous embodiment, the sleeping or reclining furniture further comprises an evaluation unit connectable to the sensor, which is set up for processing and evaluating the signals of the at least one sensor and for detecting physiological parameters of a person using the sleeping or reclining furniture. The detected physiological parameters are, for example, a heart rate, a respiratory rate, a movement behavior and/or a snoring behavior of the person. In order to be able to reliably evaluate even small signals, the evaluation unit advantageously has a filter, in particular a low-passband or bandpass filter for signal processing. Alternatively or additionally, a first signal conditioning can also take place directly at the sensor, for example by a signal amplifier and/or an analogously and/or digitally operating signal filter being arranged adjacent to the sensor or integrated in a sensor housing. A less interference-prone transmission of the measuring signal to the evaluation unit is thereby achieved.

Furthermore, the evaluation unit can have a memory for storing a time course of the physiological parameters. Alternatively or additionally, the evaluation unit may be connected to an external memory for this purpose. This can be a cloud, e.g. a storage space offered by an external service provider that is provided decentral and/or is distributed by servers that can be reached via the Internet. On the other hand, it can also be a so-called personal cloud, in which storage space is provided locally, e.g. in the form of a NAS (Network Attached Storage) that can be reached within an intranet. Finally, a mass storage connected directly to the evaluation unit via cable would also have to be understood as a cloud in this sense. Other forms of a wired cloud, include USB mass storage sticks or memory cards such as SD cards. These cloud-forming storage elements may be provided at various locations and components, e.g. also in a PC (personal computer) or a smartphone as a mobile device.

The evaluation unit can additionally have a monitoring device for comparing the physiological parameters with predetermined limit values in order to be able to warn a person in a case in which a health risk for the person itself or another person is recognized. For this purpose, the evaluation unit preferably has a transmission unit for transmitting the physiological parameters to a mobile device or another external unit. The transmission unit is preferably set up for the wireless transmission of the physiological parameters to the mobile device, in particular via a WLAN- or Bluetooth-transmission path. If the physiological parameters are transmitted to the mobile device, a comparison of the physiological parameters with predetermined limits can also be made in the mobile device. A wired connection to external units is also conceivable, for example if the external unit is a staff call system in a nursing home.

Alternatively, the monitoring device itself may be formed externally of the evaluation unit and connected to the evaluation unit. Such an external monitoring device may e.g. be formed in a mobile device. The necessary functionality can be provided via an appropriate program ("App"). The external monitoring device can also be part of an alarm control center, for example in a care facility.

In a further advantageous embodiment, the sleeping or rest furniture comprises an electromotive furniture drive with adjusting drives for adjusting furniture parts. Further, a control device for controlling the adjusting drives is provided, wherein the evaluation unit is preferably coupled to the control device or is integrated into the control device. In this way, components of the control device that are already present in the electromotive furniture drive can also be used for the evaluation unit, for example a power supply unit, communication devices and/or a housing including the connection possibilities. In addition, a wiring of the sensor simplifies when the existing structure of the electromotive furniture drive is used.

In a further advantageous refinement of the sleeping or rest furniture, the evaluation unit for the signals of the sensor is additionally set up for the detection and evaluation of vibrations and movement that occur when one or more of the adjustment drives are actuated. In this way, the at least one sensor can be used as a positive secondary benefit in order to determine a malfunction and/or an overload and/or a non-load of one or more of the adjusting drives during operation. The determined states indicate already or possibly imminent technical problems of the variable speed drives or incorrect use.

Since the respective adjustment drive is mechanically coupled to the furniture components, the sensor is able to detect even the smallest vibrations and/or noises of the respective adjustment drive. All signals in this connection are detected by the evaluation unit and classified as signals of the adjustment drives by means of suitable filters, for example suitable bandpass filters. The statements about the wear and/or noise condition of the respective adjustment drive are stored.

In a further advantageous embodiment of a sleeping or rest furniture, the evaluation unit is connected to a sound pickup for receiving airborne sound. Such a sound pickup may e.g. be formed by a condenser microphone. The detection of airborne sound can under supporting means are used, e.g. to detect snoring or to associate a snoring sound with one of several persons who are in the sleeping or rest furniture. Furthermore, the connection is at least electrically. Preferably, the sound pickup is arranged in the evaluation unit. For this purpose, it may be expedient if the sound pickup is granted access to the airborne sound to be picked up. If the evaluation unit comprises a housing, this has openings in the area of the sound pickup. Such a sound sensor is designed in particular for receiving a physiological parameter based on snoring sounds. A sleeping or rest furniture can comprise or have a plurality of such sound sensors and at least one sensor according to application.

Furthermore, further sensors for detecting structure-borne noise can be provided, which are attached to the furniture, the mattress or a furniture component. The evaluation unit is then preferably able to evaluate all sensor signals and establish a relationship by comparison between the sensor signals. If, for example, one of several people in the furniture snores and if signals from sensors to absorb structure-borne noise and signals from sensors to absorb airborne sound match, it can dearly be an assignment which one of the persons in bed actually snores.

BRIEF DESCRIPTION OF THE DRAWING

The invention will be explained in greater detail hereafter on the basis of exemplary embodiments with the aid of figures. In the figures:

FIGS. 6a, 6b each shows a detail of the embodiment of FIG. 5 in different mounting states;

DETAILED DESCRIPTION OF PREFERRED EMBODIMENTS

Figure 1:
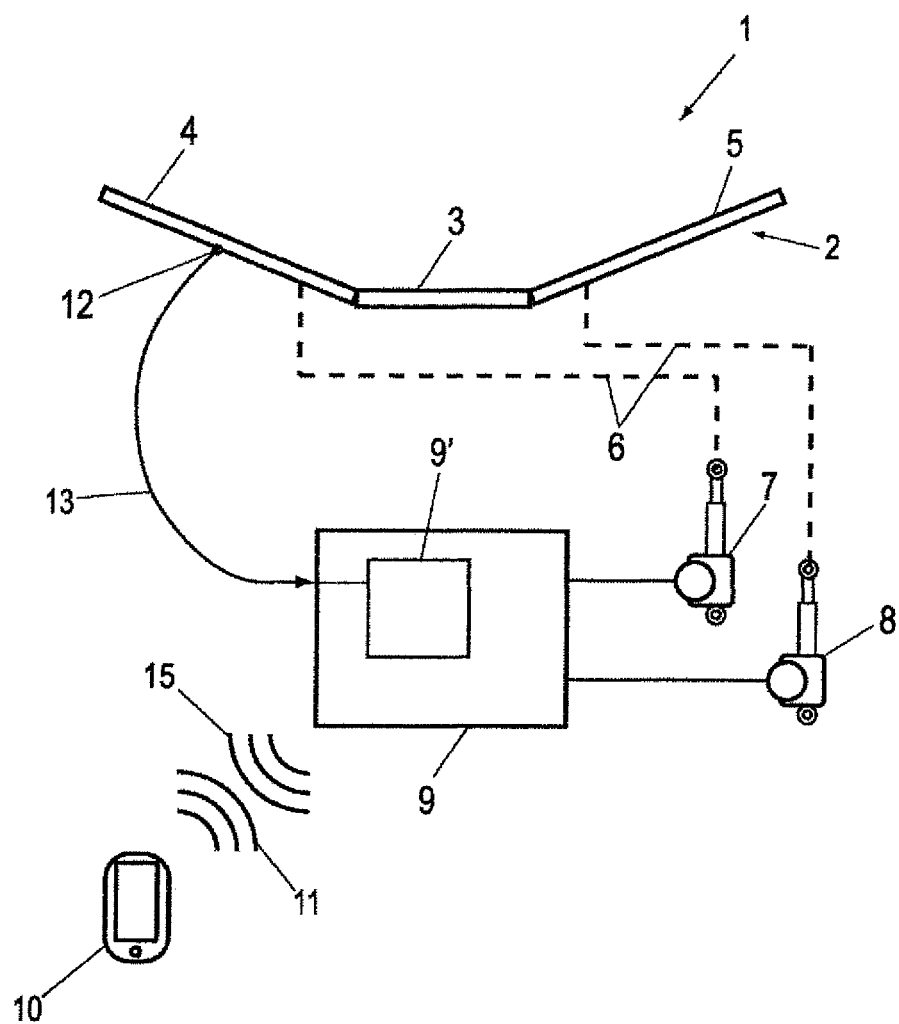
FIG. 1 shows a first exemplary embodiment of a piece of sleeping furniture comprising an electric motor furniture drive in an isometric view.

FIG. 1 shows a bed 1 as an example of sleeping furniture comprising an electric motor furniture drive.

The bed 1 has at least one support element 2 for accommodating a mattress not shown here. The bed 1 can be designed as a single bed for one person or also as a double bed for multiple persons. The support element 2 is formed from a plurality of planar parts and is placed or mounted on a base element (not shown here), e.g. a frame with feet.

In the example shown, the support element 2 has a back part 4 and a leg part 5, which are arranged so as to be movable relative to a fixed middle part 3 or relative to the base element. This movable arrangement is realized, for example, by means of a so-called motion fitting (not shown here). The movement is designed to be displaceable and/or pivotable.

The bed 1 shown in this example is equipped with an electromotive furniture drive. The movably mounted back part 4 and the leg part 5 are coupled in each case via an only schematically shown connection 6 to an electromotive adjusting drive 7, 8. Thus, the back part 4 is coupled to the electromotive adjusting drive 7. The electromotive adjusting drive 8 is provided to move or adjust the leg part 5.

The electromotive adjusting drives 7, 8 are presently designed as linear drives. The linear drives have one or more electric motors, wherein each motor is provided downstream with a speed-reducing gear with at least one gear stage. Another gear, for example in the form of a threaded spindle gear, can be provided downstream of the speed reduction gear, which generates a linear movement of an output member from the rotational movement of the motor. The last gear member or a further member connected thereto forms the output member. The output member of the respective electromotive adjusting drive communicates with the respective furniture component (back part 4, leg part 5) or alternatively with a component connected to the base element, so that during an operation of the electric motor of the respective adjusting drive 7, 8 the movable furniture components 4, 5 are adjusted relative to each other or relative to the base element.

The electromotive adjusting drives 7, 8 are connected to a control device 9. This connection can be formed, for example, as a pluggable cable connection, which is not shown here. The control device 9 has an electrical supply unit, which provides the electric power, e.g. from a power supply network, for the electromotive adjusting drives 7, 8. For this purpose, the control device 9 is connectable via a power cord, not shown in this example, to a mains plug with a mains connection. The mains plug conducts the input-side mains voltage via the power cord to the electrical supply unit of the control device 9, which supplies a low voltage on the secondary side in the form of a DC voltage.

Alternatively, the control device 9 is provided upstream with an external mains-dependent power supply with mains input and secondary-side low-voltage output, which supplies the low voltage in the form of a DC voltage via the line.

In an alternative embodiment, the control device is not arranged in a separate housing, but is integrated in one of the adjusting drives 7, 8. This adjusting drive then represents a main drive to which, if necessary, further adjusting drives can be connected.

In a further alternative embodiment of an electromotive furniture drive, the control device cart be arranged distributed in the system, such that each of the adjusting drives 7, 8 itself has a motor control and comprises a bus communication interface via which the adjusting drives 7, 8 are connected to each other and to other components. In this case, it can be provided that at least one of the adjusting drives 7, 8 has its own power supply unit for its power supply or for supplying several or all existing adjusting drives and/or possibly further system components.

A handset 10 is provided which has control elements with which the electromechanical adjusting drives 7, 8 are controllable via the control device 9. The handset 10 may be connected via a cable to the control device 9 in an embodiment. Alternatively, the handset 10 can be provided with a transmission device for a wireless transmission of signals to the control device 9. The wireless transmission can be realized by a radio transmission link, an optical transmission link (e.g. for infrared light) and/or an ultrasonic transmission link, wherein the control device 9 is equipped with a respectively corresponding receiving unit. Further alternatively, the handset can also form the control device for the adjusting drives, for example, in that the operating current of the adjusting drives is switched directly via switches of the handset.

In the illustrated exemplary embodiment, a mobile device 14 takes over the function of the handset 10. The mobile device 14 may be in particular a commercially available mobile phone ("smartphone") or a tablet computer. Preferably, a software ("app") for the function as a handset 10 is installed on the mobile device 14. Control instructions to the adjusting drives 7, 8 can be sent via a wireless transmission link 11 from the mobile device 14 used as a handset to the control device 9. The wireless transmission link 11 may for example be based on a WLAN (Wireless Local Area Network) or Bluetooth transmission path.

According to the application, a sensor 12 is provided in the illustrated bed 1, which detects vibrations, movement and/or sound. In the example shown, the sensor 12 is mounted in the vicinity of the back part 4. Details of the connection of the sensor 12 with the bed 1 are explained in more detail below in connection with FIGS. 3 to 13.

The sensor 12 is formed for example as a piezoelectric component or as an electromagnetic or electromechanical component and is sensitive to vibrations or movements of the base, to or on which it is fastened—in the present case for vibrations or movements that the frame of the back part experiences. Such vibrations include, in particular, structure-borne sound, which is picked up by a person resting in the bed 1 via the mattress by the back part and is relayed. "Movements" shall include in particular low-frequency vibrations and deflections of the sensor 12 whose frequency is in the Hertz or sub-Hertz range. A further suitable sensor is an electromechanical sensor, for example, a micromechanical acceleration sensor.

In addition, the sensor 12 can be sensitive to (airborne) sound waves and can function in this meaning as a microphone. Alternatively a separate microphone, e.g. a condenser microphone, might be present as an additional sensor for detecting airborne sound.

The sensor 12 is connected via a sensor cable 13 to an evaluation unit 9' that is arranged within the control device 9 in the present case. It is alternatively possible to form the evaluation unit 9' separately from the control device 9 in its own housing. For transmitting the determined physiological parameter the evaluation unit 9' can be connected to the control device 9. If necessary, a power supply for the sensor 12 is provided via the sensor cable 13 and signals output by the sensor 12 are relayed to the evaluation unit 9'. In an alternative embodiment, the sensor 12 can be coupled via a wireless connection, for example, a radio connection, to the control device 9. In this case, the sensor 12 is provided with a separate power supply, for example, in the form of a possibly rechargeable battery.

The evaluation unit 9' comprises, for example, amplifiers and filter units, which enable certain physical functions of a person located in the bed 1 to be inferred from the signal transmitted by the sensor 12. In particular, the evaluation unit is configured for the purpose of ascertaining physiological parameters of the person from the signals of the sensor 12. Such parameters relate, for example, to cardiac and circulatory functions and comprise, for example, a heart rate and a respiratory rate. Furthermore, it can be ascertained whether the person located in the bed is snoring. Moreover, movements of the person are detected. Details on the ascertainment of the mentioned parameters from the signals of the sensor 12 will be explained in greater detail hereafter in conjunction with FIG. 2.

The determined parameters are transmitted either immediately or after buffering in the evaluation unit 9' as wireless signals 15 to a mobile device 14. The mobile device 14 can be in particular a commercially available mobile telephone ("smart phone") or a tablet computer and is equipped with corresponding software ("app"), which enables analysis and preferably graphic display of the time dependence of the ascertained sleep parameters. WLAN (wireless local area network) or Bluetooth, for example, can be used as the transmission link for the wireless signals 15.

Moreover, a comparison of the measured physiological parameters to predefined limiting values for these parameters can be provided in the evaluation unit 9'. If the ascertained parameters are transmitted immediately, i.e., without long buffering in the evaluation unit 9', during the sleeping phase to the mobile device 14, such a comparison can alternatively or additionally take place therein. If the parameters exceed or fall below the limiting values or one or more of the parameters leave a predefined range, it is provided that the evaluation unit or the mobile device 14 outputs an alarm signal. This alarm signal can be output optically and/or acoustically directly by the evaluation unit and thus, for example, the evaluation unit 9' or the control device 9, respectively, and/or the mobile device 14. Alternatively or additionally, it can be provided that the mobile device 14 emits an alarm message via a further wireless transmission link (not shown here) (for example, WLAN, mobile radio network). In this manner, a further person can be informed if undesired sleep parameters are shown. The illustrated bed 1 and/or the electric motor furniture drive comprising the sensor 12 can thus also be used for clinical monitoring and/or for patient monitoring or for monitoring small children to protect from sudden infant death.

In the illustrated exemplary embodiment, the sensor 12 is arranged as the only sensor on a frame element of the back part 4. Furthermore, the use of multiple sensors 12, which are positioned at different points in or on the bed 1 is possible. In this case different types of sensors 12 can be positioned in the bed 1. The different sensor types show characteristic frequency ranges for which they are particularly suited. The combination of different kind of sensors allows for recording and analyzing a notably broad frequency spectrum.

Each sensor 12 is arranged at a position being ideally suited for the sensor, i.e. a position where the signal detectable by the sensor is particularly distinct. The arrangement of each sensor 12 ideally takes place in regions of the bed 1 which lie adjacent to the sound-generating body parts of the monitored person(s), i.e., for example, in the heart/lung region and in the region of the throat and/or the mouth opening. Conceivable attachment locations are the back part 4. Other attachment locations are the seat or middle part, which extends between back part 4 and leg part 5.

The connection of the sensor 12 to the evaluation unit 9' or the control device 9, respectively, which is arranged inside the bed 1, prevents the sensor cable 13 having to be laid outside the bed 1. The fixing of the sensor 12 in or on the bed 1 ensures correct positioning of the sensor 12 at all times and thus reliable analysis of the data of the sensor 12.

Figure 2:
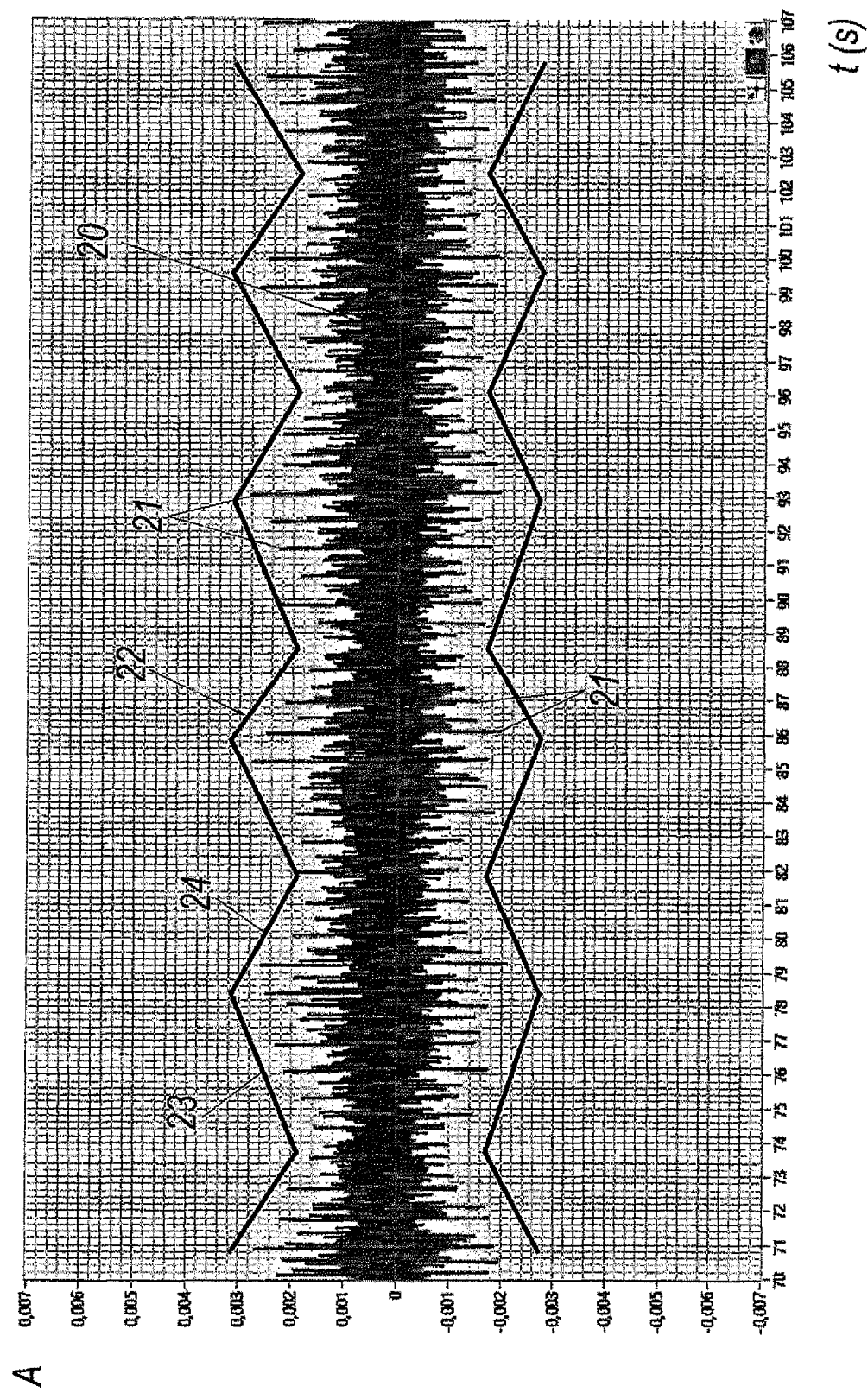
FIG. 2 shows a reproduction of a time dependence of sensor data.

FIG. 2 shows a detail of a measured signal 20 of the sensor 12 in a diagram. The time curve t in seconds is indicated on the horizontal axis. A signal amplitude A in arbitrary units is shown on the vertical axis.

The portion shown of the signal curve of the signal 20 is during a calm sleep phase without movement and without snoring of the observed person. A movement of the person is expressed in amplitudes which exceed those shown by a factor of several tens to hundreds. Movements may therefore be identified very easily. A snore and the vibrations accompanying it can also be clearly differentiated from the illustrated signal curve, since they are reflected in an amplitude greater by multiple times.

In the curve of the signal 20 shown in FIG. 2, regular peaks 21 are observable, which originate from the heartbeat of the person and are referred to as heartbeat peaks 21 hereafter. A heart rate can be ascertained from the interval of the heartbeat peaks 21. The time interval of adjacent heartbeat peaks 21 permits statements about the pulse uniformity, which can be a measure of the depth of the sleep.

Furthermore, it can be seen in FIG. 2 that the amplitude of the heartbeat peaks 21 varies regularly at a lower frequency. This variation is illustrated by an envelope curve 22. The envelope curve 22 displays alternating rising flanks 23 and falling flanks 24. The curve of the envelope curve 22 is correlated with the breathing of the person. The rising flanks 23 identify an inhalation phase and the falling flank 24 identifies an exhalation phase.

The example of FIG. 2 shows how cardiovascular parameters can be concluded from the signals of the sensor 12, in the present case pulse and respiration. In a similar manner, further sleep parameters, such as movement states and snoring, can be ascertained.

Filtering of the raw signals of the sensor 12 is carried out, in particular by means of a low-pass filter, for the analysis of the signals 20. The use of a bandpass filter having suitable base frequencies is also possible. Low-pass or bandpass filters are used to eliminate interfering frequencies. A signal-strength-dependent amplification (automatic gain control)

can also take place in this case. The processing of the signals is preferably carried out with the aid of a digital signal processor (DSP).

The sensor 12 can additionally or alternatively also be used for monitoring the correct function of the electric motor drive. An actuation of the adjusting drives 7, 8 results in a movement of the moving furniture parts, for example, of the back part 4 and/or the leg part 5. In addition, the actuation of the adjusting drives 7, 8 results in vibrations of these furniture parts and also of the entire furniture, which are also detected by the sensor 12. These vibrations occur in a typical frequency range. The signal curve reflects the motor movement of the adjusting drives 7, 8. A first typical relevant frequency range is in the range of the motor speed of the motors of the adjusting drives 7, 8. Faults on the motor itself or an output gear wheel are shown in this frequency range. A further typical relevant frequency range corresponds to an integer fraction according to a transmission ratio of the gear, which is approximately 1:30 to 1:50. Faults in downstream gear stages or roller bearings are indicated in this frequency range. A third typical frequency range is in the range of squeaking noises of hinges, which are part of a furniture fitting. Shape and amplitude are, on the one hand, typical for the adjusting drive 7, 8 used, on the other hand, they give information about the correct function of the adjusting drives 7, 8 and the wear state thereof.

An overload of one of the adjusting drives 7, 8 can also be recognized on the basis of the signal form of the signals of the sensor 12. The sensor 12 can thus function, for example, as a pinch protection, wherein the control device 9, in the event of overload of one of the adjusting drives 7, 8, stops this drive and/or causes it to run in the opposite direction. An underload on the adjusting drive 7, 8 can also be an indication of pinching, for example, if a furniture part (back part 4, leg part 5) is released and the adjusting drive 7, 8 is operated nearly without force, this indicates pinching of a body part under the moving furniture part which is sinking down. An adjusting drive 7, 8 operated without load is also identifiable on the basis of the signals of the sensor 12.

Figure 3:
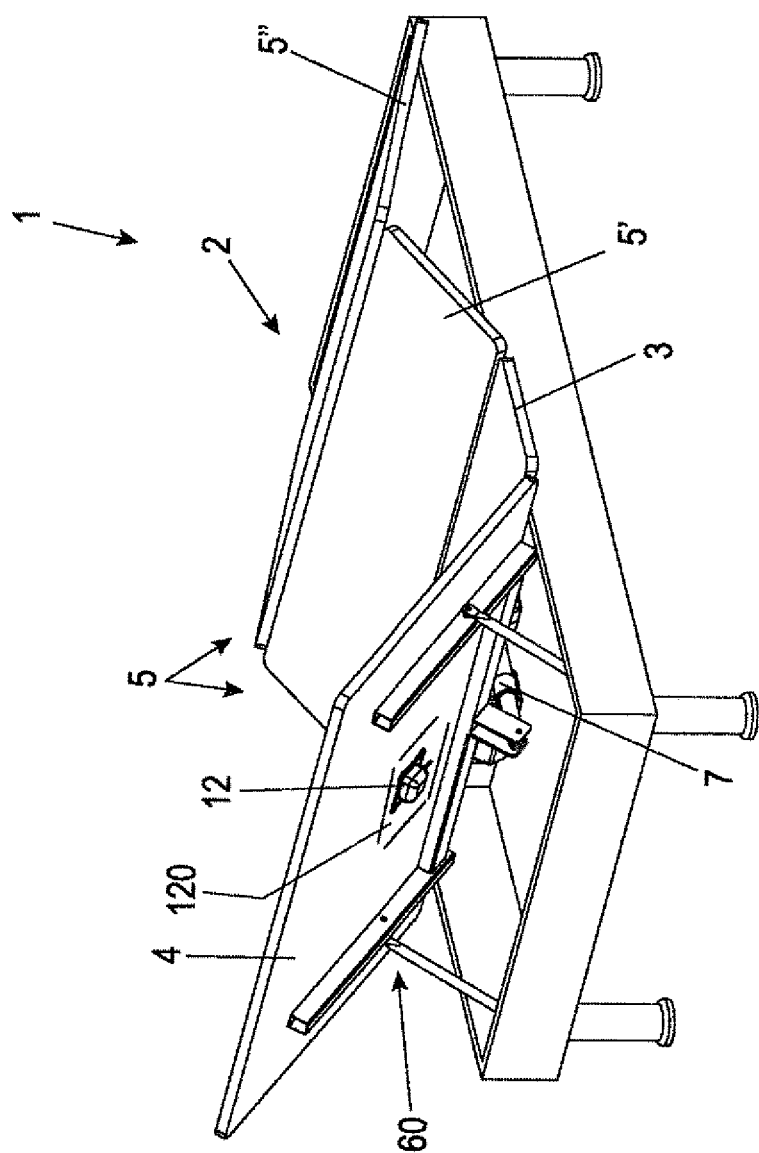
FIG. 3 shows a second exemplary embodiment of a piece of sleeping furniture comprising an electric motor furniture drive in an isometric view.
Figure 4:
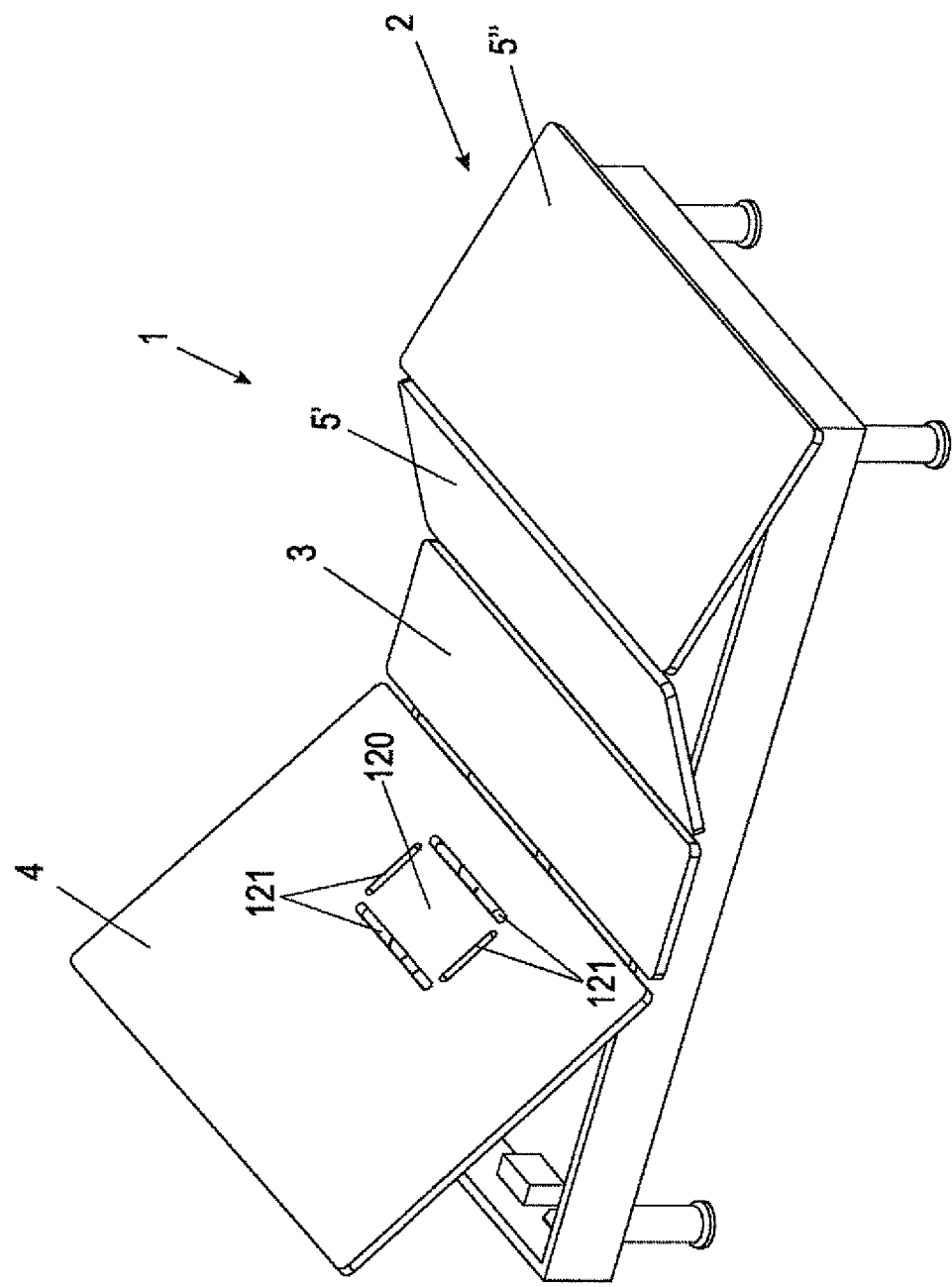
FIG. 4 piece of sleeping furniture of FIG. 3 in an isometric view diagonally from above.

In FIGS. 3 and 4, another embodiment of a bed 1 is shown as an example of a sleeping furniture with an electromotive furniture drive with adjusting drives 7, 8 and a sensor 12 for detecting vibrations, movements and/or sound. In this as well as all other embodiments, the same reference numerals designate the same or equivalent elements as in the example described above.

For reasons of clarity, a control device 9, an evaluation unit 9', a handset 10 with transmission link 11 and a mobile device 14 and the wireless signals 15 exchanged therewith, as shown in FIG. 1 are not shown in FIGS. 3 and 4.

In FIGS. 3 and 4, the bed 1 is shown in an isometric view from two different viewing directions. Again, the bed 1 has a frame with feet, which forms a base element. It is understood that instead of the frame-like base with the separately formed feet, a rather box-shaped frame with four side walls that reach to the floor may be provided.

The base element carries a support element 2 which receives a padding, in particular a mattress not shown here. Although the reproduced bed 1 is a single bed for one person, it may equally be designed as a double bed for several persons.

In the present case, the support element 2 does not have a supporting frame that e.g. carries a slatted frame as a support for the padding or the mattress, but essentially self-supporting plates. Such a bed concept is implemented, for example, in so-called box spring beds, in which the mattress is thicker than conventional mattresses and includes spring elements, which provides a sufficient sleeping comfort without a resilient pad, as for example, a slatted frame.

The support element 2 in turn has a plurality of mutually adjustable parts, specifically a non-pivoting middle part 3, a back part 4 a pivotable relative to the middle part 3 and a leg part 5, which is two-part here. A first section 5' of the leg part 5 is pivotable relative to the support element 2. A second portion 5" of the leg part 5 is pivotally connected to a free transverse side of the first portion 5' with the first portion 5' and is accordingly raised with the first portion 5' at the connecting line of the two sections 5',5".

Along the connecting lines between the non-pivoting central part 3 and the back part 4 and the first portion 5' of the leg part 5, and at the connecting line between the first and the second portion 5',5" of the leg part 5 pivot fittings, e.g. in the form of hinge strips are arranged. A U-shaped frame is screwed onto the back part 4 as a movement-fitting 60 for transmitting power, the base of which extends in the transverse direction of the bed 1 in the region of the connection between the back part 4 and middle part 3. The movement-fitting 60 takes the function of the connection 6 between the adjusting drive 7 and the back part 4 shown in FIG. 1. The middle part 3 is in the present case at a fixed distance to the base element.

The bed 1 of FIG. 3 is shown in an isometric oblique view obliquely from above in FIG. 4. In this figure, it can be seen that in the region of the sensor 12, which is not visible here, four cuts 121 arranged in a rectangular manner surround a section 120 of the back part 4 from the remaining region of the back part 4. Through the cuts 121, this section 120 is acoustically, i.e. with regard to its ability to vibrate, decoupled from the rest of the back part 4. The sensor 12 is mounted on the back of this decoupled section 120. The decoupled section 120 is therefore also referred to below as the sensor plate 120. At each corners of the sensor plate 120 there only remain relatively narrow webs between the cuts 121.

The decoupling offers the advantage that the sensor plate 120 forms an oscillatory system relative to the back part 4, which acts as an antenna for structure-borne and airborne sound and transmits it to the sensor 12. The sensor plate 120 effectively represents an enlarged receiving membrane for the sensor 12. Accordingly, a large oscillation amplitude can form on the sensor plate 120, which leads to a strong signal of the sensor 12. The positioning of the sensor plate 120 in the lower back region is advantageous, since signals which are usually caused by respiration and heartbeat of a person are most clearly detected in this region.

The sensor plate 120, which acts as an antenna, thus has the function of receiving physiological signals, such as respiratory signals, cardiac signals, movement signals, snore signals, from the person in the furniture or in bed 1 in the form of vibrations or sound and providing it to the at least one sensor 12. The antenna or the sensor plate 120 can thus be understood at least as a signal receiving unit. It is also designed as a signal forwarding unit. For optimum reception and/or forwarding of the signals, the sensor plate 120 is formed from a suitable material which has a low attenuation. Furthermore, the geometry of the sensor plate 120 is designed to be effectively sound-optimized. Material and/or geometry are chosen so that a passage and a forwarding of sound and/or vibration to the respective sensor 12 occurs possibly without damping. The materials used are solid wood-based materials and wood-fiber materials. The use of plastics is also conceivable, wherein a fiber reinforcement of the material promotes advantageous sound properties. A use of metal such as aluminum is also conceivable.

Another geometric embodiment of a sensor plate 120 provides a molded from a plastic spatial body. Another geometrical configuration of a sensor plate 120 provides a planar body formed from a wood fiber material.

Figure 5:
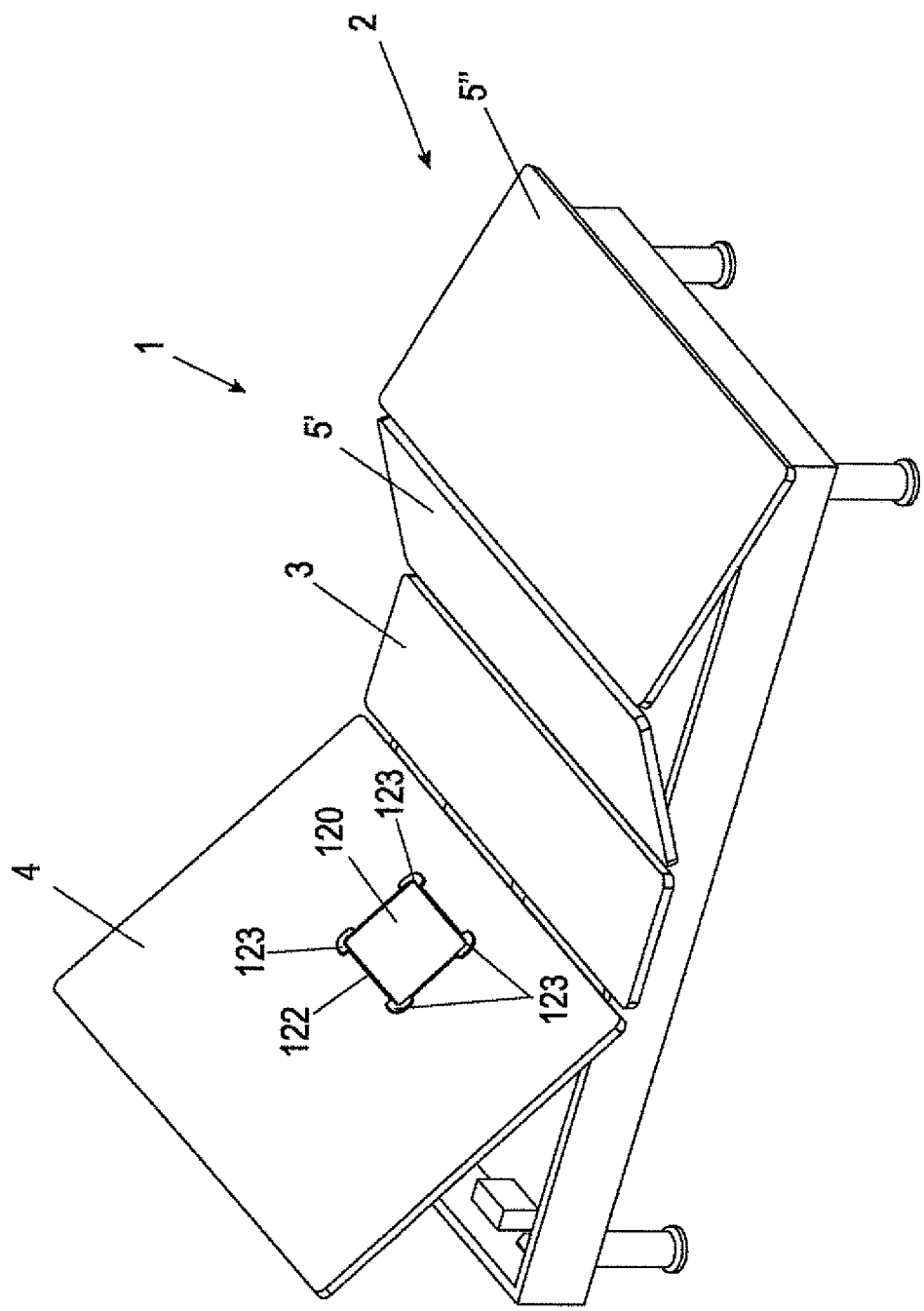
FIG. 5 shows a third exemplary embodiment of a piece of sleeping furniture comprising an electric motor furniture drive and a sensor in an isometric view.

FIG. 5 shows another embodiment of a bed as sleeping or reclining furniture with a sensor 12, which in turn is located below a sensor plate 12 arranged in a back part 4.

In contrast to the exemplary embodiment of FIG. 4, in the embodiment of FIG. 5, a circumferential cut 122 is formed around the sensor plate 120. The sensor plate 120 is thus not connected with the back part 4 by remaining webs as in the embodiment of FIG. 4. In order to bear the sensor plate 120 on the back part 4, holding elements 123 are arranged in the four corners of the sensor plate 120, which are preferably made of an elastic material such as a soft plastic or a silicone or rubber. The properties of the holding elements 123 can be selectively adjusted to achieve a preferred vibration behavior of the sensor plate 120.

In FIGS. 6a and 6b, the arrangement of the sensor plate 120 and the holding elements 123 is shown in more detail in an isometric drawing. FIG. 6a shows the holding elements 123 separated from the sensor plate 120, whereas FIG. 6b shows the sensor plate 120 with attached holding elements 123. The unit of sensor plate 1:20 and holding elements 123 of FIG. 6b is then inserted into a correspondingly shaped section of the back part 4.

Figure 7:
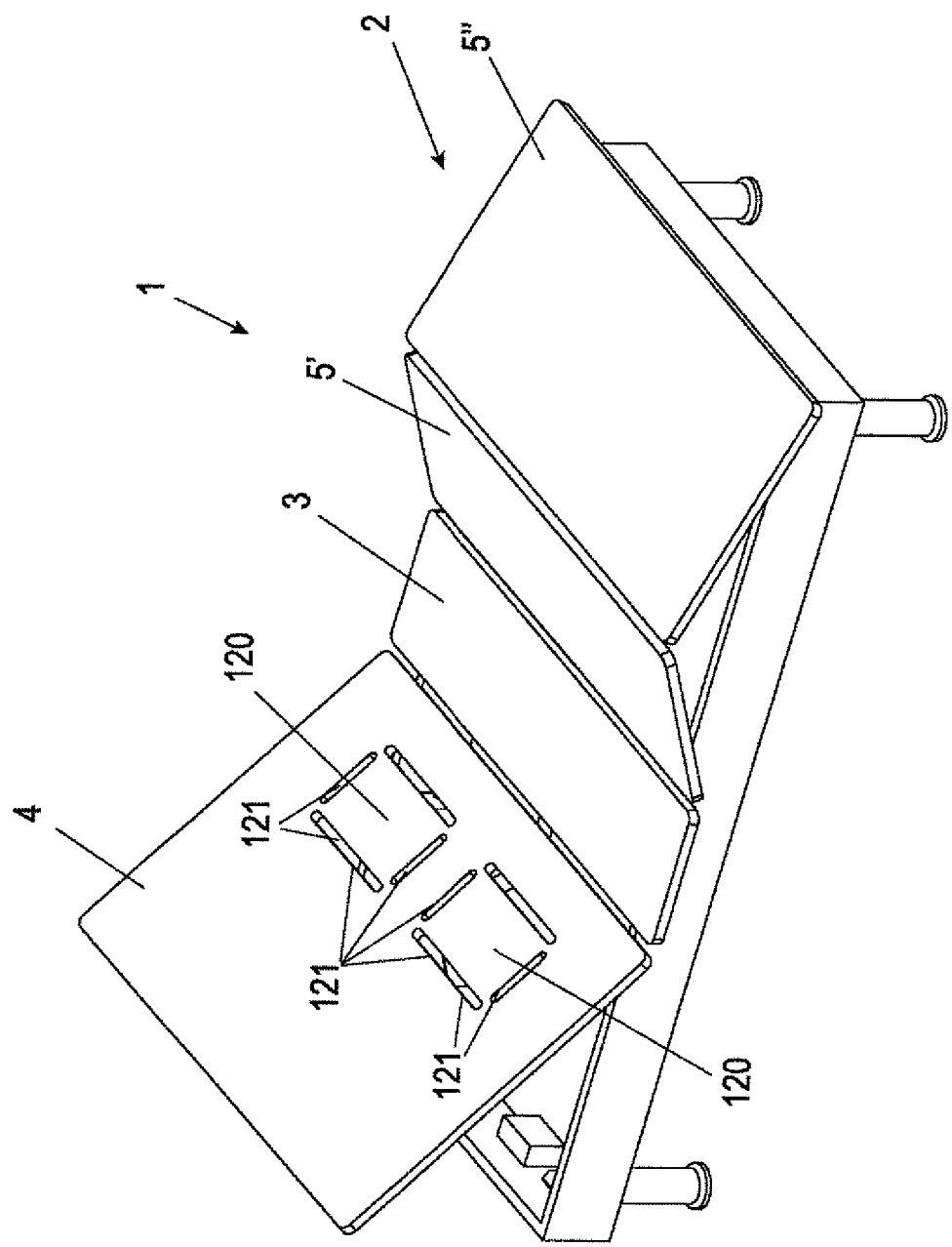
FIGS. 7-12 each shows a further exemplary embodiment of a piece of sleeping furniture comprising an electric motor furniture drive and a sensor in each case in an isometric view.
Figure 8:
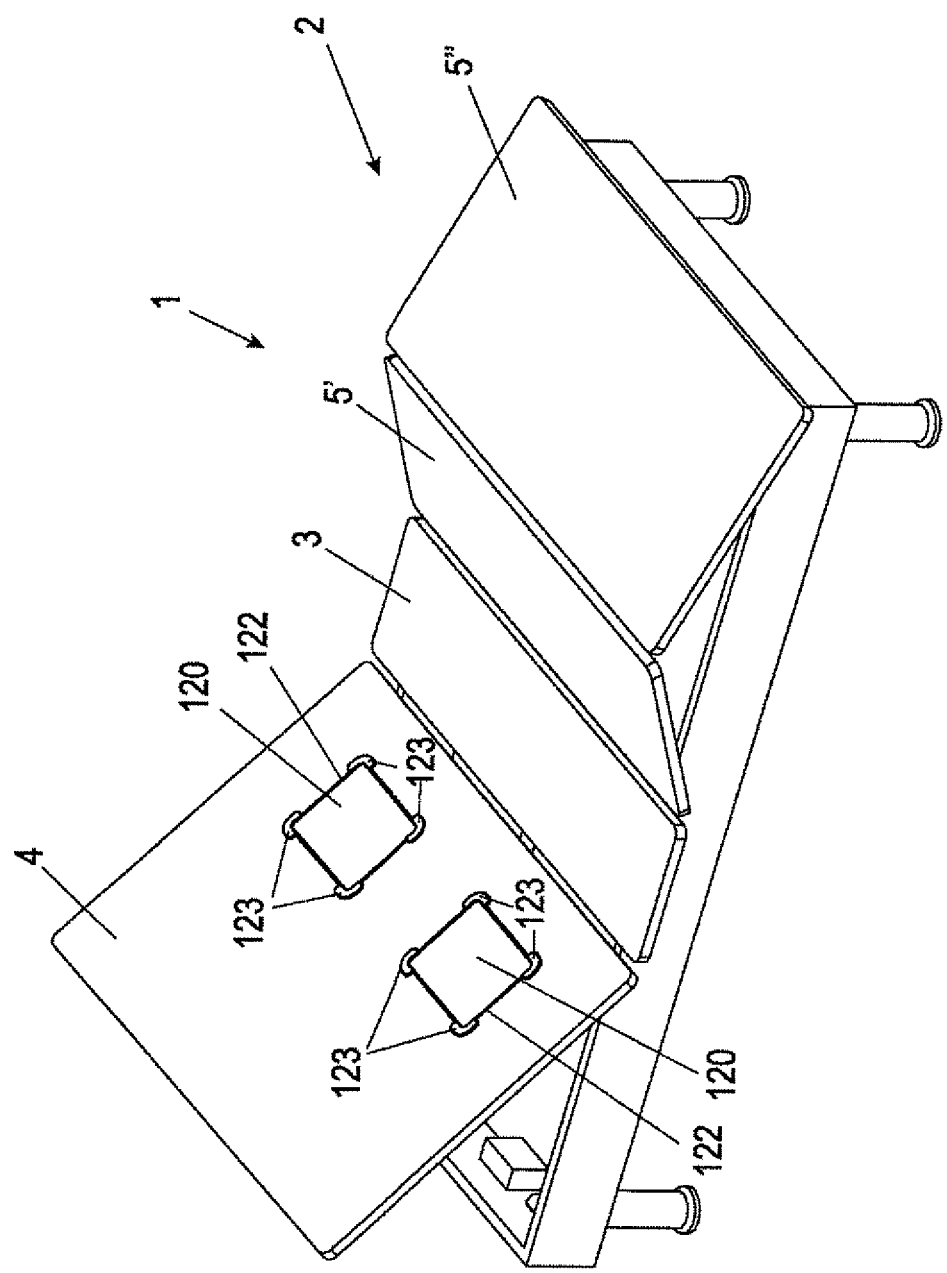
Figure 9:
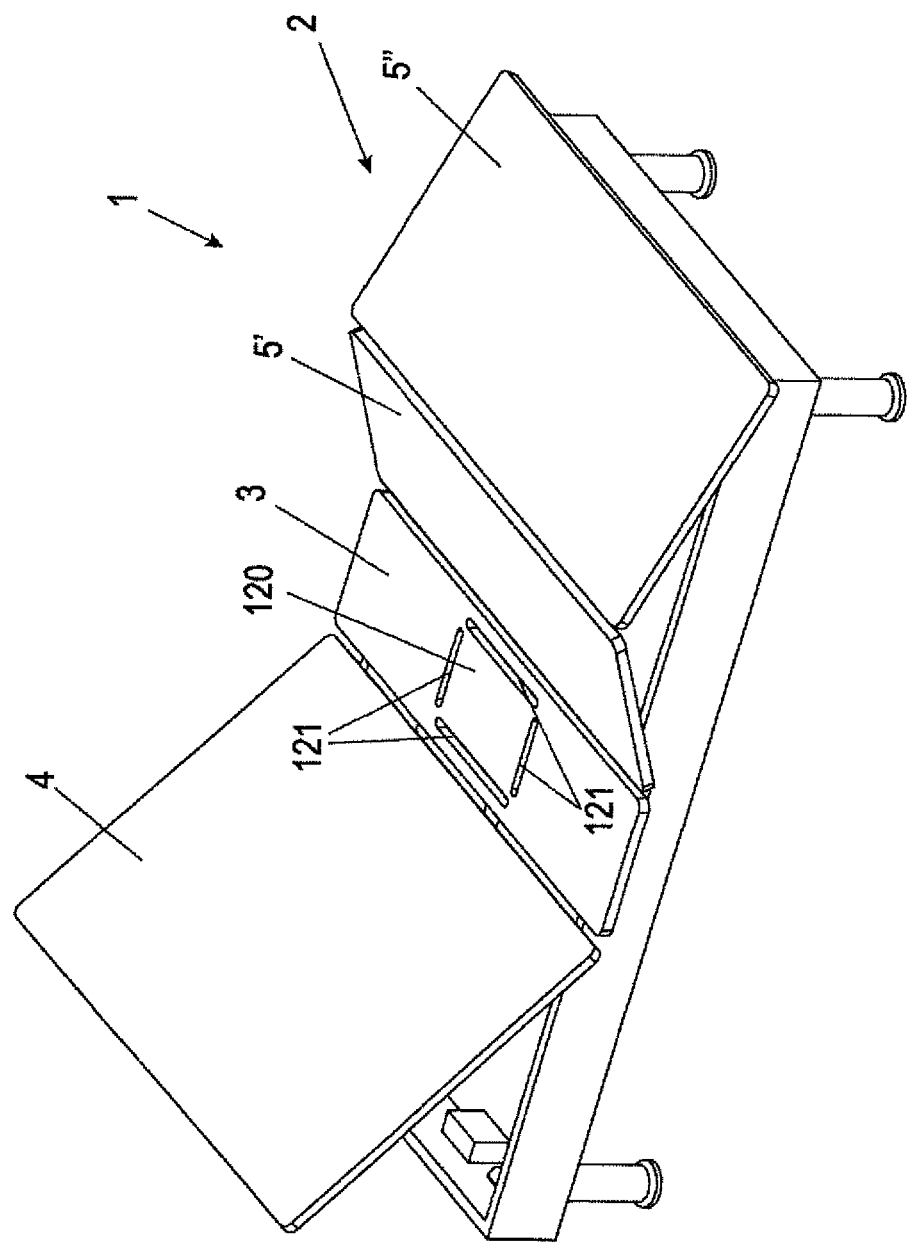
Figure 10:
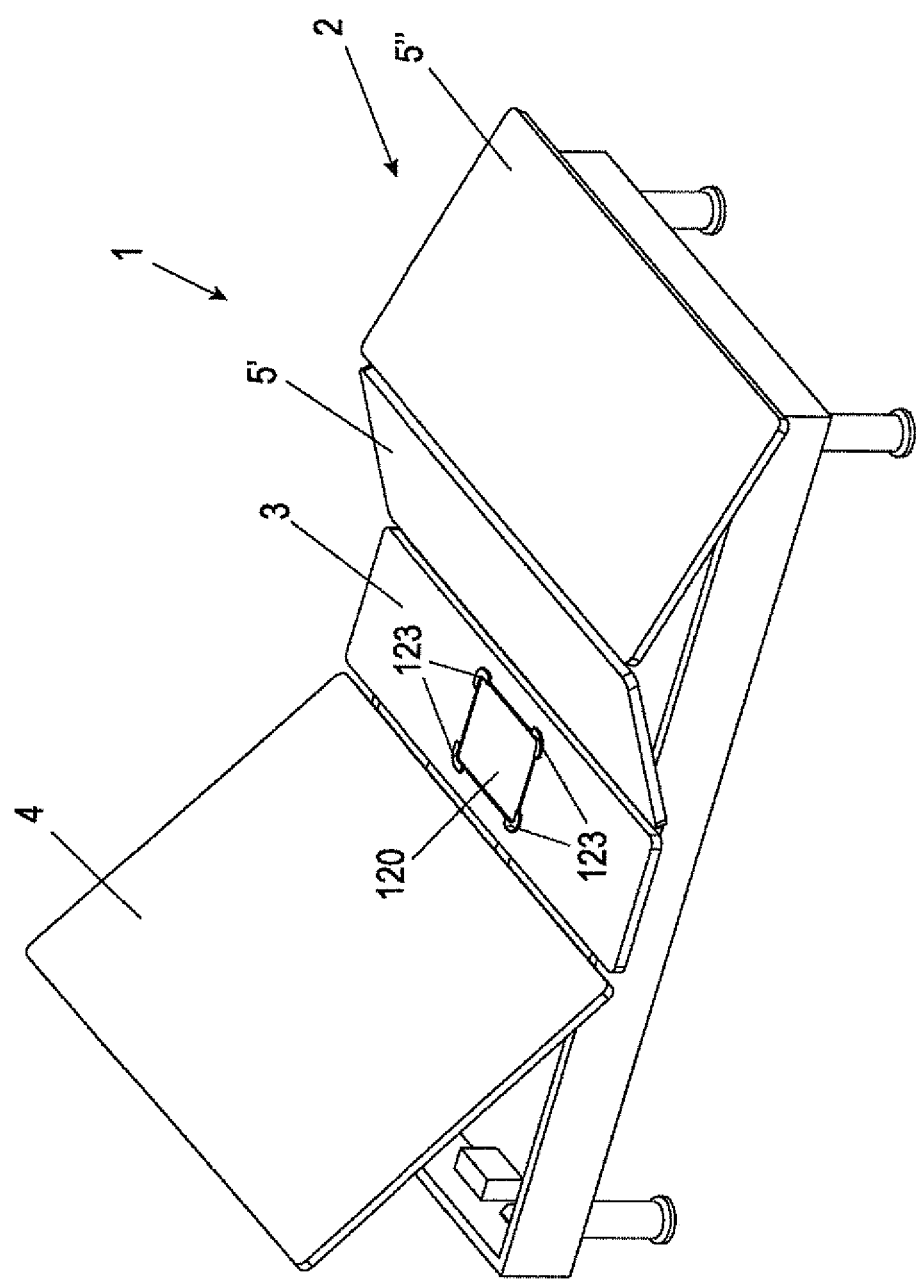

Two further embodiments of a bed 1 as an example of a sleeping and reclining furniture are shown in FIGS. 7 and 8 in the same manner as in FIGS. 4 and 5. In these two embodiments, a single sensor plate 120 is not centrally located in the lower third of the back part 4, but two separate juxtaposed sensor plates 120 are each provided in the lower left and lower right lower half of the back part 4, This arrangement serves the most independent possible detection of sleep noise and vibration or movement and thus physiological parameters of two person lying side by side in the bed 1. In the embodiment of FIG. 7, sections of the back part 4 that are separated, but not completely cut-off by cuts 121, are designed as sensor plates 120. A separate sensor 12 is mounted on each of these sensor plates 120. In the exemplary embodiment of FIG. 8, analogous to the example of FIG. 5, sensor plates 120 are arranged in a circumferential cut 122 by holding elements 123. Here too, a separate sensor 12 is provided on each sensor plate 120 in each case. The illustrated arrangement with two sensor plates 120 and two sensors 12 can also be used in a single bed 1, wherein the sensor signals of the individual sensors 12 are either averaged or the respective stronger signal of one of the sensors 12 is taken into account, depending on how the person lies in bed 1.

FIGS. 9 to 12 show four further exemplary embodiments of a bed 1 as an example of a sleeping or reclining furniture according to the invention.

In these exemplary embodiments, the sensor plate 120 or the sensor plates 120 are not arranged in the back part 4 but in the middle part 3. It has been found in tests that also in the area of the middle part 3, in which the lower back or the buttocks of a person is positioned in sleep, is also very well suited to absorb sleep sounds, movements and vibrations that allow to derive physiological parameters. The middle part 3 can be arranged fixedly standing with respect to a frame of the bed 1. In so-called "wall hugger" beds, the middle part 3 is moved in the direction of the head end of the bed 1 if the back part 4 is pivoted, in order to prevent a gap between the back part 4 and a wall adjacent to the head part of the bed. Alternatively, a slight pivoting of the central part 3 is conceivable.

An advantage of the arrangement of the sensor plate 120 or a plurality of sensor plates 120 on the middle part 3 is that the load due to the weight of the person(s) resting in the bed 1 is substantially constant, regardless of the setting of the back part 4 or the leg part 5. The mechanical boundary conditions influence the sensor 12 or the decoupling of the sensor plate 120. The more constant the boundary conditions are, the more clearly the measured signals of the sensor 12 can be evaluated.

Figure 11:
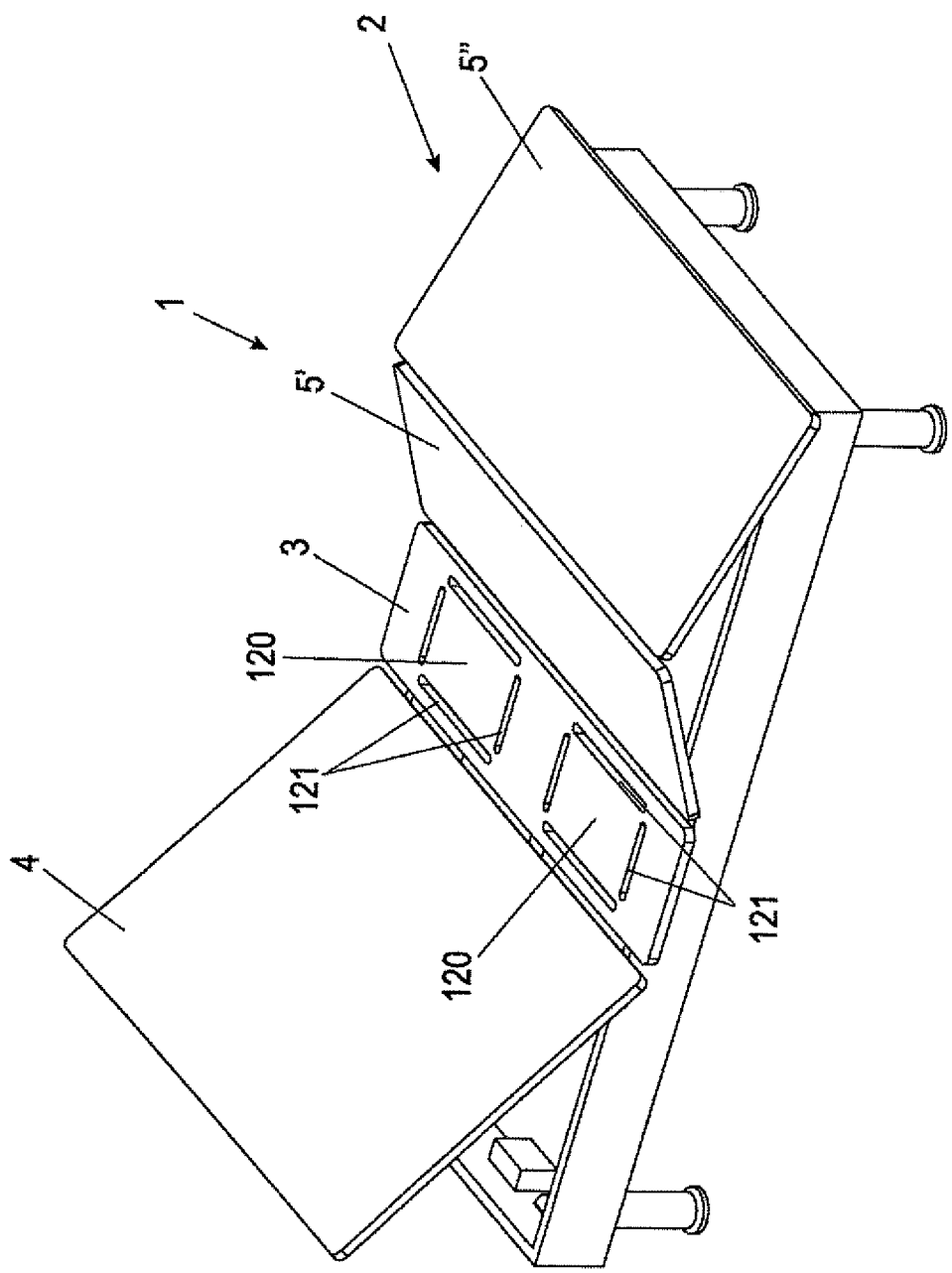
Figure 12:
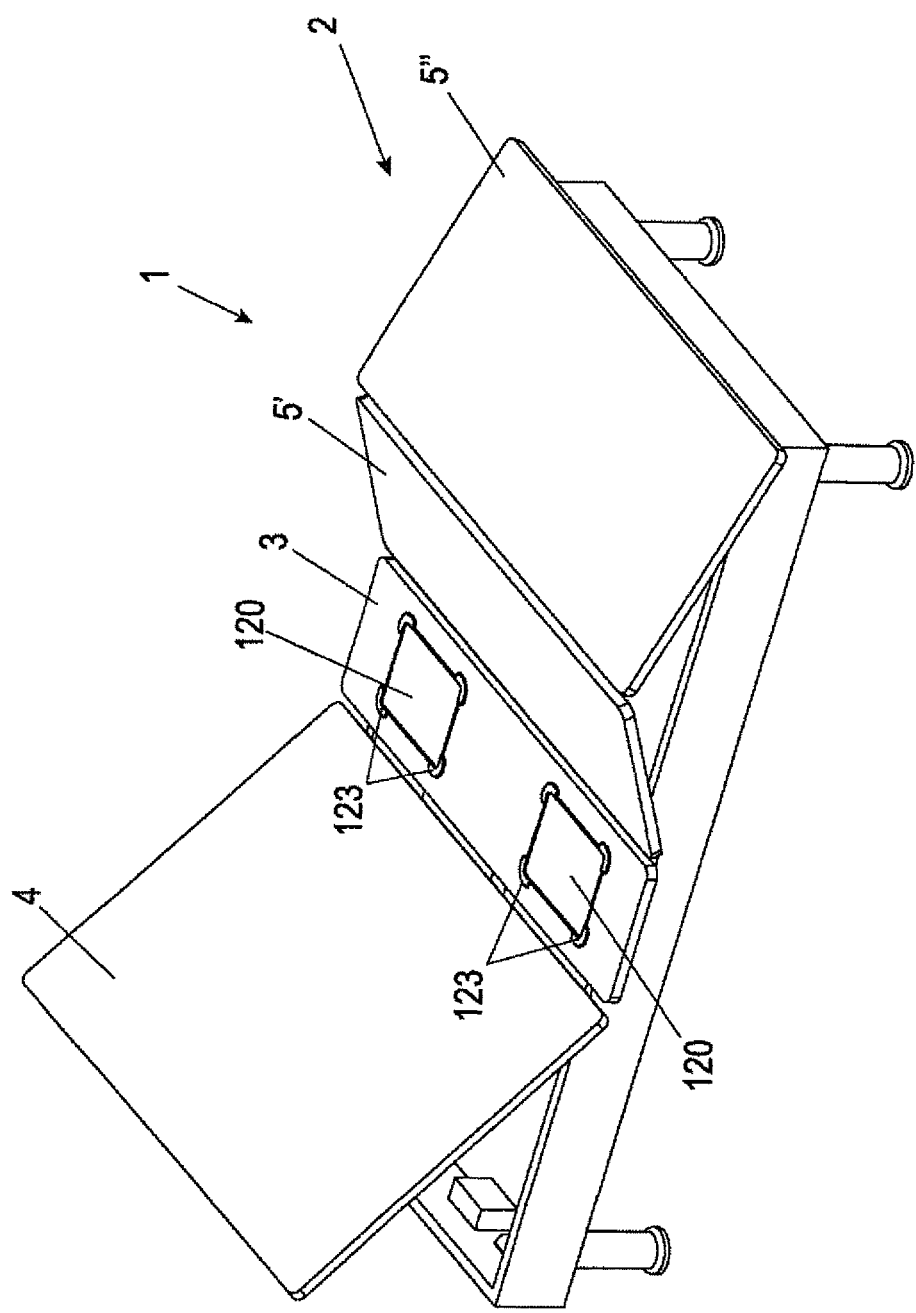

In the illustrated embodiments, a central sensor plate 120 with associated sensor 12 are provided either analogously to the FIGS. 4 and 5, or in each case 2 juxtaposed in the examples of FIGS. 11 and 12. Again, the different types of decoupling of the sensor plate 120 can be used, namely the introduction of slot-like, not interconnected cuts 121 in the embodiments according to FIGS. 9 and 11 or the introduction of a circumferential cut 122 and the use of holding elements 123 in the exemplary embodiments of the FIGS. 10 and 12.

Figure 13:
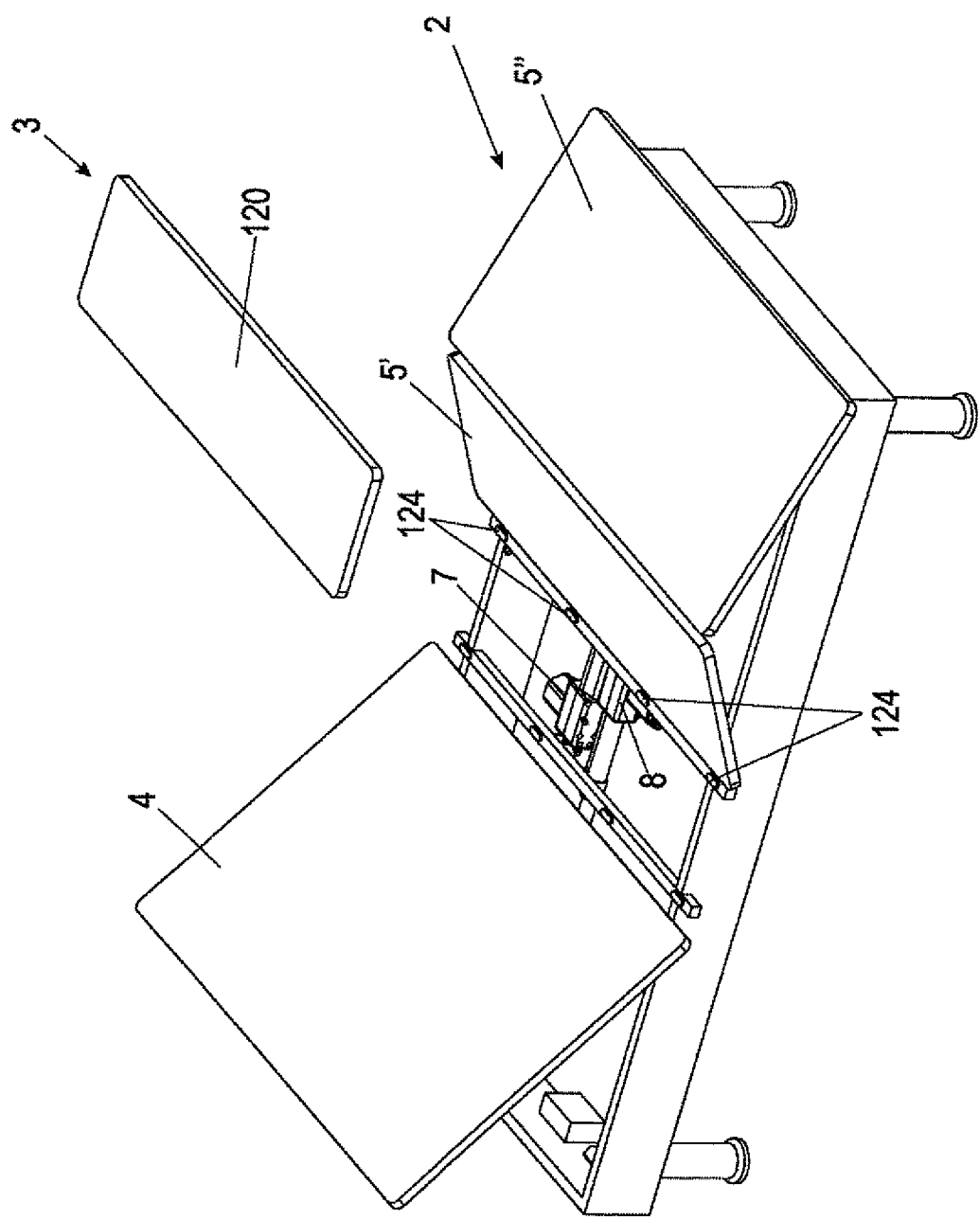
FIG. 13 shows a further exemplary embodiment of a piece of sleeping furniture comprising an electric motor furniture drive and a sensor in an isometric view in a partly mounted state.

In the middle part 3, which is not moveable in the examples shown and is not coupled to one of the adjusting motors 7, 8, a further method for signal amplification can be used. This is shown in FIG. 13. Since the middle part 3 is not coupled to the movement-fitting and compared with the back part 4 and the leg parts 5 'and 5' rather small, the entire central part 3 is used as the sensor plate 120 in this embodiment.

In order to achieve an antenna effect also in this case, the middle part 3 is mounted on elastic elements 124 (buffers), which consist of an elastic and soft material such as rubber or silicone or a soft plastic and which allow vibrations of the middle part 3 with respect to the support frame 2. In FIG. 13, the central part 3 is shown lifted off to show the elastic members 124 and their arrangement.

In all of the exemplary embodiments illustrated above, a transmission of vibrations, in particular of structure-borne sound, from the decoupled section 120 or from the sensor plate 120 to the sensor 12 with minimized losses is important. The sensor 12 and the decoupled section 120 and the sensor plate 120 each have a connection for the transmission of airborne sound and/or structure-borne sound and/or vibrations.

Preferably, the connection is fixed. Alternatively, the connection is substance-conclusive. Furthermore, the connection preferably allows no relative movements between sensor 12 and sensor plate 120. In an advantageous manner, the damping of the transmission of the sound or vibrations to the sensor 12 is thereby very small or approaches zero. For example, a connection of the sensor 12 on the sensor plate 120 is suitable by gluing. As an adhesive, a possibly multi-component liquid adhesive or alternatively a film adhesive can be used. A film adhesive may e.g. an adhesive strip with adhesive film applied on both sides. Further, the connection may include primers or the like with which the sensor plate 120 and/or the sensor 12 is provided prior to the bonding operation.

According to a further embodiment, the connection is material-conclusive such that the sensor 12 forms an inseparable unit. Such a cohesive or compressed unit can be done by casting or potting. Ideally, the sensor 12 is arranged in a recess of the sensor plate 120 and potted with this by means of a potting compound. Alternatively, the sensor 12 may be cast on the surface of the sensor plate 120 by means of the described potting compound or be poured downright.

According to a further embodiment, the connection is provided by a force-fit. In this case, the sensor 12 is fixed in the direction of the sensor plate 120 by means of a permanently pressurizing force. Here, the sensor 12 can contact the sensor plate 120 directly. Preferably, however, a sensor housing is provided, which receives the sensor 12, and at least its electrical connection. Ideally, the sensor housing with the sensor plate 120 is assembled in a way that the sensor 12 enters into a firm connection with the sensor plate even after completion of the joining process. Furthermore, combinations of the aforementioned connections may exist. The addition of a sensor housing is in principle of advantage because it protects the sensor 12 and can perform a cable strain relief. Thus, as an alternative, a cover housing can protectively cover a sensor 12 firmly bonded to the sensor plate 120 and have a strain relief for the connection cable of the sensor 12. The respective housing is also firmly connected to the sensor plate 120 by screws, for example.

Figure 14:
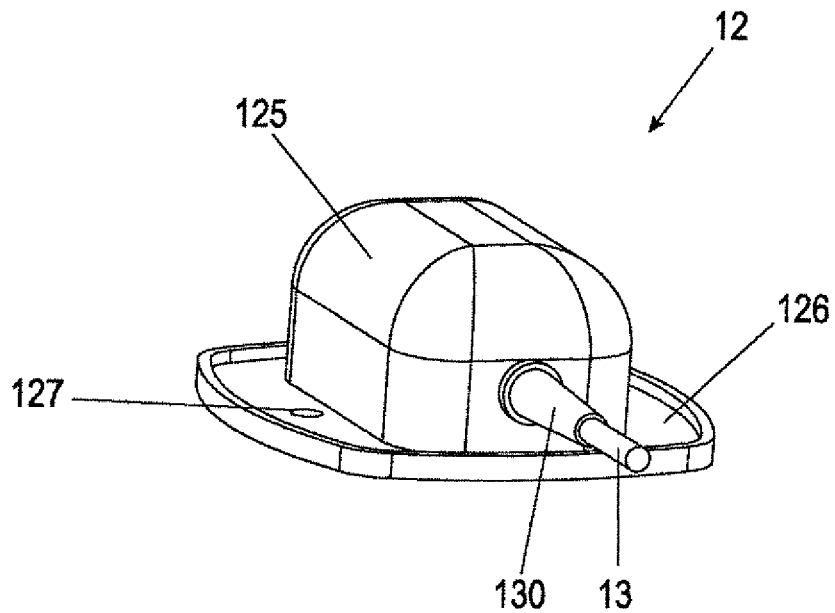
FIGS. 14 and 15 each show an isometric illustration of a sensor having a sensor housing from various viewing directions.
Figure 15:
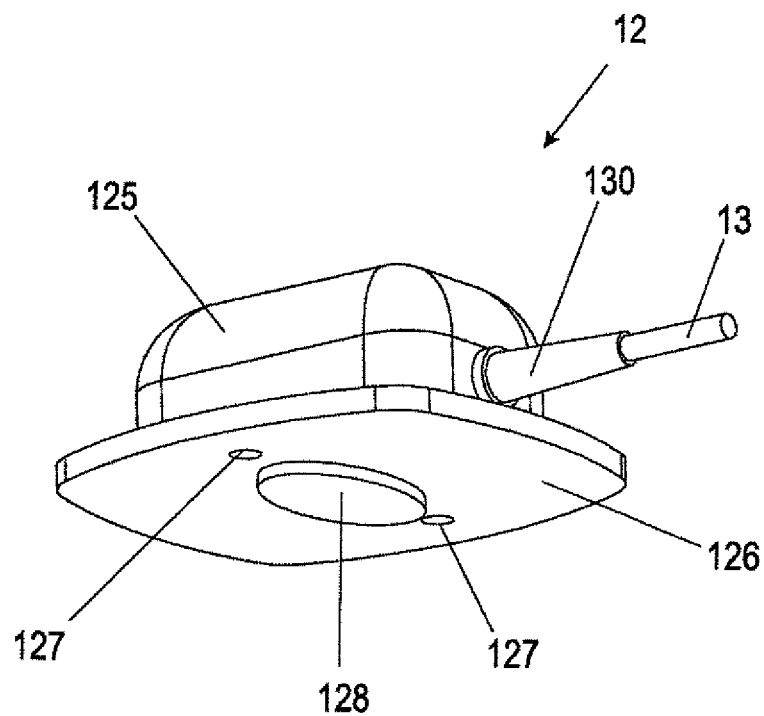

An example of a suitable sensor housing 125 of a sensor is shown in an isometric view in FIGS. 14 and 15. This sensor 12 may be used for example in the embodiments shown in FIGS. 3 to 12 and can also be seen in the example of FIG. 3.

The sensor housing 125 is shown in an oblique view on its upper side in FIG. 14 and in an oblique view with respect to its underside in FIG. 15.

The sensor housing 125 comprises a dome-shaped housing upper part, in which the actual sound or vibration pick-up sensor is arranged. A cable bushing 130, preferably with kink protection, is used to guide the sensor cable 13. The dome-shaped housing part is arranged centrally on a mounting plate 126. This has mounting holes 127, example, for a screw mounting.

As can be seen in FIG. 15, an elevation 128 is arranged on the underside of the mounting plate 126, which faces the furniture part, for example the back part 4, with which the sensor 12 abuts against this surface when mounted on a flat surface. A vibration transmission thus takes place in particular in the region of the elevation 128. In the interior of the sensor housing 125, the actual sound or vibration transducer (pick-up) with its vibration-sensitive area is preferably arranged above the elevation 128. If necessary, the elevation 128 can be continued inwards, so that there is a direct transfer to the vibration-sensitive section of the sound or vibration sensor. In this way, structure-borne sound is transmitted as directly as possible to the sound or vibration sensor.

In addition, sufficient space for electronics is present in the housing 121 so that a signal processing of the sensor signal can take place directly in the sensor housing 121. This signal processing can include amplification and/or filtering of the signal emitted by the sound or vibration sensor. Corresponding power supply lines for the evaluation electronics in the sensor housing 121 may be provided in the sensor cable 13. In addition to electronics for signal preprocessing, the evaluation unit 9' described above can also be arranged directly in the sensor housing 121.

According to a further embodiment, the sensor 12 is integrated into the sensor plate 120 during the manufacturing process. In the case of a sensor plate 120 formed from a plastic, the sensor 12 can be cast into the sensor plate 120 in the production process of the sensor plate 120. In a sensor plate 120 molded from a fiber-wood material, the sensor 12 is integrated during the manufacturing process of the sensor plate 120. In the case of a sensor plate 120 formed from a layered wood-based material, the sensor 12 is glued or laminated into the sensor plate 120 during the production process of the sensor plate 120.

Figure 16:
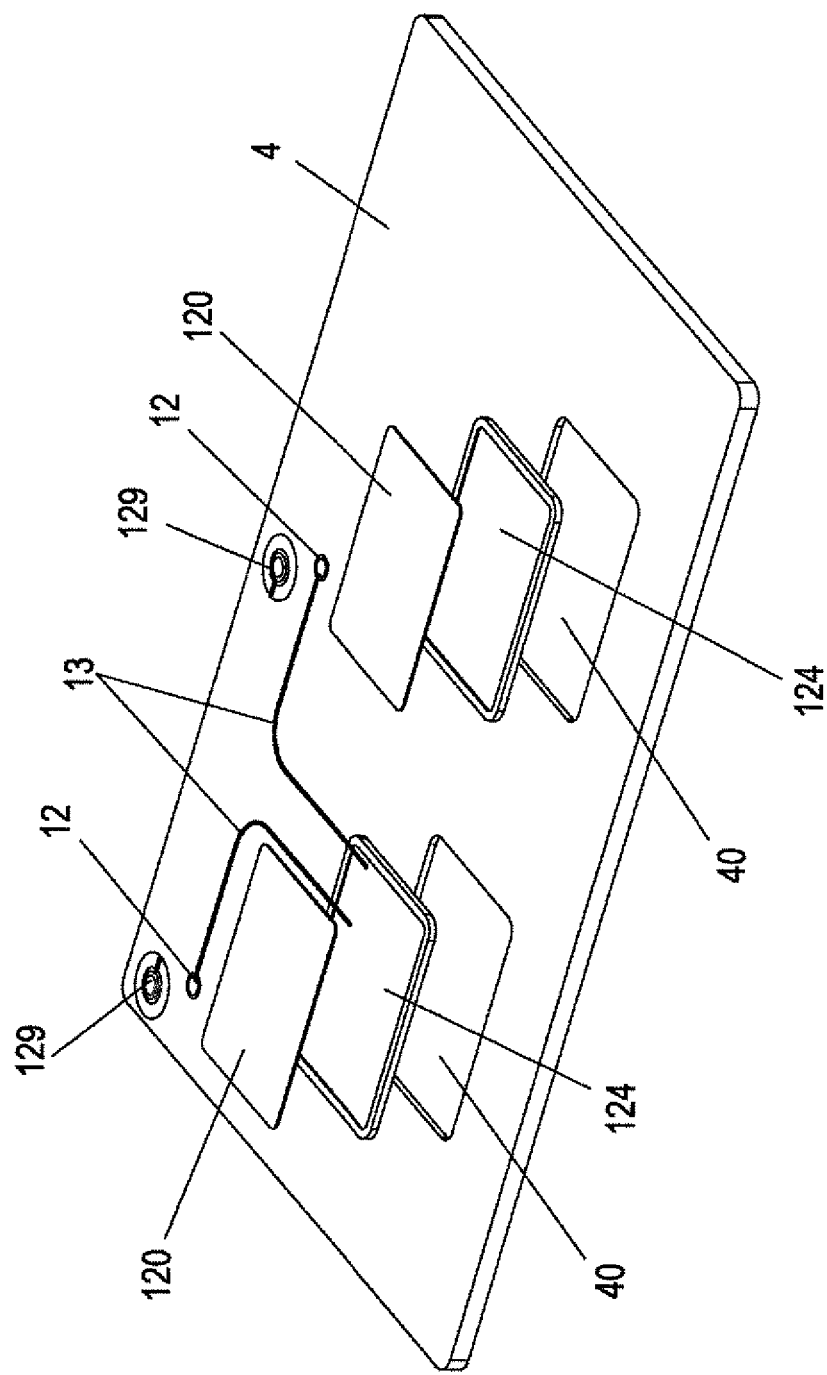
FIG. 16 shows an isometric explosion view of a part of a piece of sleeping furniture having sensors.

Alternatively, a metallic or plastic sensor plate 120 can also be used. FIG. 16 shows an arrangement of—in this case—two sensors 12 each on a sensor plate 120 at a plate-shaped element of a sleeping or reclining furniture, by way of example the back part 4 of the embodiments described above.

In this back part 4 in the illustrated embodiment, two-dimensional depressions 40 are introduced, in each of which a here likewise substantially flat elastic element 124 is inserted. The elastic member 124 may be made of, for example, a soft rubber or sponge rubber or silicone material. It has an upwardly projecting peripheral edge, which forms a lateral boundary for an inserted sensor plate 120. The sensor plate 120 is preferably made of a hard material, for example aluminum or a hard plastic or even steel. Bonding of the elastic member 124 with the back part 4 on the one hand and the sensor plate 120 on the other hand is preferably carried out by adhesive. On this sensor plate 120, the sensor 12 is applied in the form of a piezoelectric element, also preferably glued. On the sensor 12, a protective cover 129 is placed, preferably also glued. At the same time, this protective cover 129 serves to fix the sensor cable 13, which in the present case is guided over the surface of the back part 4. Alternatively, the sensor cable 13 could also be guided through a hole to the other side of the back part 4. The hole can either run directly next to the sensor plate 120 through the back part 4, or can run, in the region of the sensor plate 120 through the sensor plate 120, the elastic element 124 and the back part 4.

Figure 17:
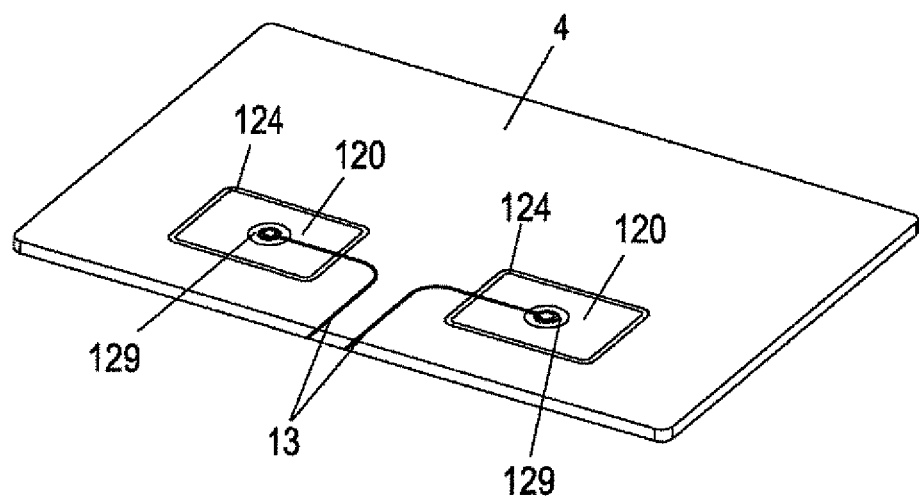
FIG. 17 shows the part of the piece of sleeping furniture with sensors in a mounted state in an isometric view.

FIG. 17 shows the arrangement in the assembled state. As in the previously described exemplary embodiments, the sensor plates 120 serve as sound-decoupling sections of the support element 2, which in particular pick-up structure-borne noise and forward it to the respective sensor 12. The sensors 12 themselves are hidden in FIG. 17 under the protective covers 129 and are not visible.

Unlike the embodiments shown so far, in the example of FIGS. 16 and 17, the sensor plates 120 are turned towards an applied mattress. The elastic elements 124 decouple the sensor 12 from interfering influences, e.g. of impact sound transmitted via a support frame or stand of the bed 1. In addition, they bundle the structure-borne sound of a person resting in bed 1 and being transmitted via the mattress and act in this sense as antenna-elements for the sensor 12.

In the arrangement shown, the sensor 12 is arranged centrally on the sensor plate 120, However, off-center positioning is also possible. Furthermore, it is also conceivable that the sensor 12 is arranged outside a main surface of the sensor plate 120, e.g. on an tongue or tab that projects outward from the main surface of the sensor plate 120. This can reinforce the sensor signal, at least in selected frequency ranges.

In order to protect the arrangement, in addition to the protective covers 129, it may be provided to cover the entire back section 4 with a protective material. In box spring beds such a lining of the plate-shaped support elements is basically provided.

Figure 18:
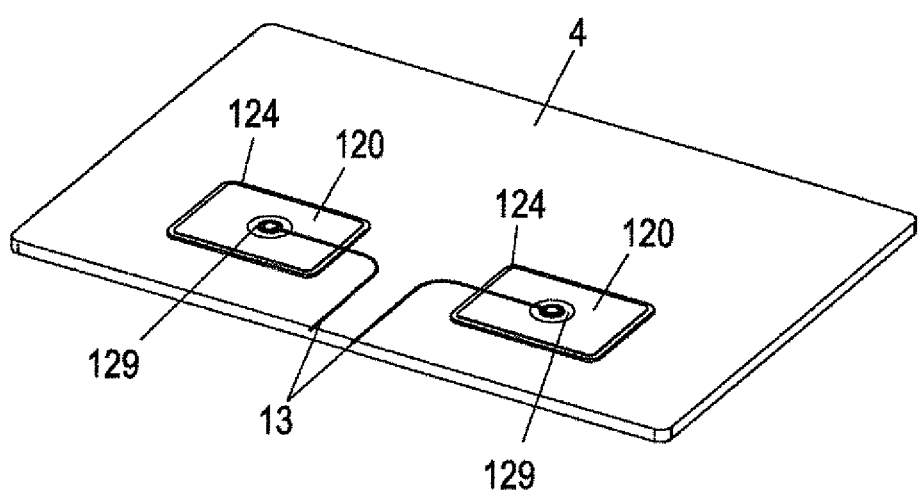
FIG. 18 shows a further exemplary embodiment of a piece of sleeping furniture with sensors in a view as in FIG. 17.

FIG. 18 shows an alternative embodiment of the back part 4 from FIGS. 16 and 17. In contrast to the embodiment of FIGS. 16 and 17, no depressions 40 are provided for receiving the sensor arrangement. The elastic elements 124 are glued directly to the surface of the back part and therefore protrude slightly over its surface.

What is claimed is:

1. A piece of sleeping or reclining furniture, comprising:
a support element configured to apply to a padding or a mattress;
a plate-shaped section made of a material identical to a material of the support element and separated from the support element by a plurality of cuts extending along a periphery of the plate-shaped section in a rectangular pattern, leaving between adjacent cuts a web to acoustically decouple the plate-shaped section from the support element, said web being made of the material and connecting the plate shaped section to the support element, with the web being arranged at a corner of the plate-shaped section, each cut having a width that is less than a length of the cut and each web having a width that is less than the length of the adjacent cuts; and
a sensor arranged on or in the plate-shaped section and configured to detect vibration, movement, or sound applied to the plate-shaped section.

2. The piece of sleeping or reclining furniture of claim 1, wherein the plate-shaped part is a middle part of the support element.

3. The piece of sleeping or reclining furniture of claim 1, further comprising an evaluation unit connectable to the sensor and configured to process and evaluate a signal generated by the sensor and to detect a physiological parameter of a person using the sleeping or reclining furniture.

4. The piece of sleeping or reclining furniture of claim 3, wherein the detected physiological parameter is a heart rate, a respiratory rate, a movement behavior or a snoring behavior of the person.

5. The piece of sleeping or reclining furniture of claim 3, wherein the evaluation unit includes a filter for signal processing.

6. The piece of sleeping or reclining furniture of claim 5, wherein, the filter is a low-pass filter or a bandpass filter.

7. The piece of sleeping or reclining furniture of claim 3, further comprising an electromotive furniture drive including adjusting drives for adjusting furniture parts; and a control device configured to control the adjusting drives, said evaluation unit being coupled to the control device or integrated into the control device.

8. The piece of sleeping or reclining furniture of claim 7, wherein the evaluation unit is configured to detect and evaluate vibration and movement that occur when at least one of the adjustment drives is actuated.

9. The piece of sleeping or reclining furniture of claim 7, wherein the evaluation unit is configured to determine a malfunction or an overload or a non-load of at least one of the adjusting drives during operation.

10. The piece of sleeping or reclining furniture of claim 1, wherein the sensor is bonded to the plate-shaped section.

* * * * *